US010308965B2

(12) United States Patent
Lippmeier et al.

(10) Patent No.: US 10,308,965 B2
(45) Date of Patent: *Jun. 4, 2019

(54) BIOLOGICAL OILS AND PRODUCTION AND USES THEREOF

(71) Applicant: DSM IP Assets B.V., Te Heerlen (NL)

(72) Inventors: James Casey Lippmeier, Columbia, MD (US); Joseph W. Pfeifer, III, Westminster, MD (US); Jon Milton Hansen, III, Chandler, AZ (US); Kirk E. Apt, Ellicott City, MD (US); William Robert Barclay, Boulder, CO (US); Paul Warren Behrens, Ellicott City, MD (US); David Christian Martin, Reisterstown, MD (US)

(73) Assignee: DSM IP Assets B.V., TE Heerlen (NL)

(*) Notice: Subject to any disclaimer, the term of this patent is extended or adjusted under 35 U.S.C. 154(b) by 0 days.

This patent is subject to a terminal disclaimer.

(21) Appl. No.: 15/237,988

(22) Filed: Aug. 16, 2016

(65) Prior Publication Data

US 2016/0355851 A1    Dec. 8, 2016

Related U.S. Application Data

(63) Continuation of application No. 13/401,521, filed on Feb. 21, 2012, now Pat. No. 9,453,172, which is a continuation of application No. 12/230,921, filed on Sep. 8, 2008, now abandoned.

(60) Provisional application No. 60/960,037, filed on Sep. 12, 2007.

(51) Int. Cl.
*C12P 7/64* (2006.01)
*C10L 1/02* (2006.01)

(52) U.S. Cl.
CPC .......... *C12P 7/6472* (2013.01); *C10L 1/02* (2013.01); *C10L 1/026* (2013.01); *C12P 7/649* (2013.01); *C10L 2200/0469* (2013.01); *C10L 2270/026* (2013.01); *C10L 2270/04* (2013.01); *C10L 2290/26* (2013.01); *Y02E 50/13* (2013.01); *Y02P 30/20* (2015.11)

(58) Field of Classification Search
CPC ..................................................... C12P 7/6427
See application file for complete search history.

(56) References Cited

U.S. PATENT DOCUMENTS

| 5,340,594 | A  | * | 8/1994  | Barclay ........... A61K 31/20 426/49 |
| 9,453,172 | B2 | * | 9/2016  | Lippmeier ............ C10L 1/02 |
| 2004/0235127 | A1 | * | 11/2004 | Metz ................. A23D 7/001 435/183 |

OTHER PUBLICATIONS

Chisti, Encyclopedia of Food Microbiology, R. Robinson, C. Batt & P. Patel, Eds., Fermentation (Industrial), 1999, Academic Press, London, pp. 663-674.*

(Continued)

*Primary Examiner* — Rosanne Kosson
(74) *Attorney, Agent, or Firm* — Shannon McGarrah; Xi Chen

(57) ABSTRACT

The present invention provides biological oils and methods and uses thereof. The biological oils are preferably produced by heterotrophic fermentation of one or more microorganisms using cellulose-containing feedstock as a main source of carbon. The present invention also provides methods of producing lipid-based biofuels and food, nutritional, and pharmaceutical products using the biological oils.

15 Claims, 5 Drawing Sheets

(56) References Cited

OTHER PUBLICATIONS

Zhao, Yi, Microbial Oils and Their Potential for Application in Biodiesel, Chinese Petroleum and Chemical Science and Technology Information Guide, 2006, 159-162, 2.

\* cited by examiner

# BIOLOGICAL OILS AND PRODUCTION AND USES THEREOF

CROSS REFERENCE TO RELATED APPLICATION

This application is a continuation of U.S. application Ser. No. 13/401,521, filed Feb. 21, 2012, which is a continuation of U.S. application Ser. No. 12/230,921, filed Sep. 8, 2008, which claims the benefit of priority under 35 U.S.C. § 119(e) of U.S. Provisional Application No. 60/960,037, filed Sep. 12, 2007, the disclosure of which are incorporated by reference herein in their entirety.

FIELD OF THE INVENTION

The present invention relates to biological oils and uses and production thereof. The biological oils of the present invention can be produced by fermentation of a microorganism, preferably using a cellulose-containing feedstock. The present invention also relates to methods of producing lipid-based biofuels and fuel additives, and food, nutritional, and pharmaceutical products using these biological oils.

BACKGROUND OF THE INVENTION

The production of biological oils from sources such as plants (including oilseeds), microorganisms, and animals is essential for various purposes. For example, the production of biodiesel requires large quantities of biological oils. Biodiesel has been proposed as a carbon-neutral liquid fuel alternative to petroleum-derived diesel. Biodiesel is most commonly formed by the transesterification of acyl groups of vegetable oil lipids using a simple alcohol (such as methanol, ethanol, or isopropanol). The resulting alkyl esters can then be burned directly in most modern compression ignition engines without any mechanical modifications. Energy density of biodiesel has been estimated at 95% of that for petroleum diesel (or "fossil diesel"). However, the higher lubricity of biodiesel (and thus improved fuel efficiency) results in approximately equal mileage obtained from equivalent volumes of either fossil- or biodiesel.

Since biodiesel is currently made primarily from the seed oils of $CO_2$-fixing plants, the fuel is considered "carbon-neutral" in that all of the $CO_2$ emitted from burning biodiesel was already in the atmosphere recently as opposed to fossil diesel which when burned, releases carbon that has not been in the atmosphere for millions of years. Therefore, biodiesel and other carbon-neutral fuels may have much to contribute to world-wide efforts to reduce the emission of greenhouse gasses (such as $CO_2$).

Several states in the United States have mandated that biodiesel be mixed with fossil diesel sold in that state and the federal government has also set goals for the use of renewable transportation fuel. Current supplies of vegetable oils for conversion to biodiesel have had trouble meeting these mandate levels, resulting in higher prices for many oilseed crops, particularly soybeans. If current trends continue, prices of important oilseed crops could rise significantly. Ultimately the goal is to supplant all sources of fossil fuels with competitively priced bio-based alternatives. Unfortunately, if current sources of oil for biodiesel do not change significantly, this goal may never be realized.

Recognizing this challenge, investigations have been conducted on alternative sources of oil for biodiesel production, including the feasibility of making biodiesel from photosynthetic algae grown in open ponds. Since some algae are oleaginous and grow very quickly (for some, the duration of time from inoculum to harvest is less than two weeks), the theoretical yield of oil per acre per year could be orders of magnitude greater than what could be derived from higher plants. It should be noted that the small portions of the seeds of most oil-producing higher plants represent only a small fraction of the overall mass of the plant, whereas photosynthetic microalgae might accumulate a higher percentage of their mass as oil useful for biodiesel production. There are however, serious problems with the photosynthetic algae technology that prevent the massive scale-up which are required to compete effectively with fossil diesel technology.

The photosynthetic microalgae often had to be supplemented with $CO_2$ in order to achieve high yields of oil. From the perspective of bioremediation, this is actually a benefit as excess $CO_2$ released from coal or oil-fired electrical plants, which would otherwise be released to the atmosphere, could be used as a feedstock for making biodiesel. This approach obviously does not produce a truly carbon neutral fuel as the $CO_2$ from a coal plant is still released to the atmosphere eventually (after the biodiesel is burned), but it does delay the rate at which fossil-derived $CO_2$ is released and generates more useful energy per unit mass of fossil fuel. In fact, several companies have been established to capitalize on this technology, including Greenfuels Inc. Greenfuels specifically uses closed photobioreactor systems which dissolve very high levels of $CO_2$ from fossil-fuel-fired electrical plants into photosynthetic algal cultures. Due to the biophysical limitations of self-shading, accumulation of biomass is dependent upon total illuminated surface area. Thus, many photobioreactors are required to produce even limited quantities of biodiesel. Therefore, while this technology is useful as a bioremediation strategy for sequestering carbon (and other greenhouse gases) from fossil-fuel burning electrical plants, it is unlikely scalable to the levels required to meet future biodiesel demands.

To address the issues of scalability, other organizations have opted to further develop open pond technologies for making phototrophic, algal-derived biodiesel. Open pond systems also rely on $CO_2$ supplementation for hypothetically economical levels of oil accumulation. Therefore these systems also may be better regarded as systems for bioremediation of waste carbon from fossil fuels. The yields per acre per year of useful oil from these systems are orders of magnitude greater than what can be derived from seed-oil crops. From most perspectives, these systems appear to be the best answer to limited supplies of biodiesel oil. However, there is a significant problem which has not yet been addressed. While the absolute theoretical yields of oil per acre per year are quite high, the actual density of biomass accumulated in open pond systems is relatively dilute. Because of this, massive volumes of culture media need to be processed to extract the oil from the biomass, which could significantly increase the costs of the final oil.

A path to the replacement of gasoline with renewable alternatives such as ethanol is less complex. It should be noted, however, that the markets for compression combustion engines (which burn fossil diesel or biodiesel) and for ignition combustion engines (which burn gasoline or ethanol) generally serve different needs. Compression ignition engines offer superior torque, which make them more useful in industrial applications over ignition combustion engines, which offer greater acceleration (thus making the latter more popular for general commuting). Hence, there is no reason to expect that the ignition combustion engine could fully replace the compression combustion engine should a renewable replacement for gasoline ever be fully adopted.

Despite certain disadvantages, much has been made of the potential for ethanol to supplant gasoline as a liquid transportation fuel. The Brazilian model, which relies on sugarcane as a feedstock for ethanol fermentation, has been often cited as a pioneering example for bio-fuel viability. Unfortunately, the United States does not have a climate that could support the kind of sugarcane productivity needed for massive ethanol production. Initial efforts at scaling up American ethanol fermentation have used corn syrup and corn starch as a feedstock, but there is controversy surrounding the sustainability and scalability of this arrangement as well. Because of this, more recent efforts have focused on "cellulosic" sources of sugars to use as feedstocks in ethanol fermentation. Cellulosic feedstock can be any feedstock containing cellulose.

Because most plants are primarily composed of structural polysaccharides (cellulose and hemicellulose) and lignan, acreage can be used more efficiently if the sugar monomers of cellulose and other structural polysaccharides are mobilized as a feedstock for ethanol fermentation. This is in contrast to using corn starch, which is found only in the corn plant kernels and constitute a relatively low percentage of the crop's dry weight. Additionally, since all plants contain cellulose, much faster-growing and more climate-tolerant plants can be used as the primary source of cellulose-based sugar. Examples of such plants include Switchgrass, *Miscanthus gigantus*, and Poplar.

Today's primary biodiesel crops use land in a similarly inefficient way (as corn for ethanol) since only the oil from the seeds of biodiesel crops is used to make biodiesel. Cellulosic ethanol processes have yet to be adopted on a broad scale but thus far cellulosic ethanol is widely accepted as a possible sustainable and economically competitive alternative to gasoline. Cellulosic feedstocks are already being considered for the manufacture of other petroleum-derived products (like plastics).

Patent application publication nos. WO 2005/035693, US 2005/0112735, WO 2007/027633, WO 2006/127512, US 2007/0099278, US 2007/0089356, and WO 2008/067605, the contents of which are incorporated herein by reference in their entirety, all relate to biodiesel or biofuel production systems.

Recently, heterotrophic growth of the microalga *Chlorella protothecoides* by fermentation has been investigated for purposes of biodiesel production. Researchers at Tsinghua University in Beijing, China have performed studies on biodiesel production using oil from the heterotrophic microalga *Chlorella protothecoides*. In these studies, microalgae are grown in fermentors using glucose or corn powder hydrolysate as sources of carbon. Microalgal oil is then extracted and transesterified to produce biodiesel. See Miao, X. and Wu, Q., *Bioresource Technology* 97: 841-846 (2006); Xu, H. et al., *Journal of Biotechnology* 126: 499-507 (2006). Although these researchers have suggested that starch and cellulose hydrolyzed solutions can be a low cost substitute for glucose as a carbon source in the fermentation process, they have also suggested that cellulose hydrolyzation is difficult and costly. See Li, X. et al., "Large-scale biodiesel production from microalga *Chlorella protothecoids* through heterotrophic cultivation in bioreactors," *Biotechnology and Bioengineering*, Accepted Preprint, Accepted Apr. 20, 2007.

In addition to diesel, another oil-based fuel that is in need of a renewable and sustainable source is jet fuel. Aircrafts depend on the use of various types of jet fuels, including kerosene-type jet fuels and naphtha-type jet fuels. The heavy reliance of the aviation industry on the limited supply of petroleum-based jet fuels creates an urgent need for the discovery of renewable jet biofuels.

Therefore, there exists a need for a low-cost and efficient method for producing lipid-based biofuels that can be easily scaled up to replace fossil diesel and jet fuels. As used herein, "lipid-based biofuel" refers to any fuel that is produced from a biological oil of the present invention, including, but not limited to, biodiesel, jet biofuels, and specialty fuels. In order to satisfy this need, an inexpensive and simple method must be developed for producing biological oils which can be converted to lipid-based biofuels. To reduce the costs of lipid-based biofuels production, there exists a need for a low-cost method of producing biological oils through the use of abundant and inexpensive raw materials, such as cellulose-containing feedstock as a main carbon source. In addition to a need to use inexpensive raw materials, there exists a need for improved processes that also target cost reduction in the production of biological oils. The improved methods of producing these biological oils will not only lower the cost of lipid-based biofuels production, but will also reduce the costs associated with the use of these biological oils in many other applications, including food, nutritional, and pharmaceutical products.

For example, it is desirable to increase the dietary intake of many beneficial nutrients found in biological oils. Particularly beneficial nutrients include fatty acids such as omega-3 and omega-6 long chain polyunsaturated fatty acids (LC-PUFAs) and esters thereof. Omega-3 PUFAs are recognized as important dietary compounds for preventing arteriosclerosis and coronary heart disease, for alleviating inflammatory conditions and for retarding the growth of tumor cells. Omega-6 PUFAs serve not only as structural lipids in the human body, but also as precursors for a number of factors in inflammation, such as prostaglandins, leukotrienes, and oxylipins. Long chain omega-3 and the omega-6 PUFAs represent important classes of PUFAs.

There are two main series or families of LC-PUFAs, depending on the position of the double bond closest to the methyl end of the fatty acid: the omega-3 series contains a double bond at the third carbon, while the omega-6 series has no double bond until the sixth carbon. Thus, docosahexaenoic acid ("DHA") has a chain length of 22 carbons with 6 double bonds beginning with the third carbon from the methyl end and is designated "22:6 n-3". Other important omega-3 LC-PUFAs include eicosapentaenoic acid ("EPA"), which is designated "20:5 n-3," and omega-3 docosapentaenoic acid ("DPA n-3"), which is designated "22:5 n-3." Important omega-6 LC-PUFAs include arachidonic acid ("ARA"), which is designated "20:4 n-6," and omega-6 docosapentaenoic acid ("DPA n-6"), which is designated "22:5 n-6."

Because humans and many other animals cannot directly synthesize omega-3 and omega-6 essential fatty acids, they must be obtained in the diet. Traditional dietary sources of PUFAs include vegetable oils, marine animal oils, fish oils and oilseeds. In addition, oils produced by certain microorganisms have been found to be rich in LC-PUFAs. In order to reduce the costs associated with the production of dietary sources of PUFAs, there exists a need for a low-cost and efficient method of producing biological oils containing PUFAs. To lower the costs of PUFA containing biological oils, there exists a need to develop a method of producing these biological oils using inexpensive raw materials (such as cellulose-containing feedstock) and improved processes that are designed to lower the costs of production.

SUMMARY OF THE INVENTION

The present invention provides a method for producing a biological oil comprising growing a microorganism of the kingdom Stramenopile by heterotrophic fermentation using feedstock comprising cellulose as a carbon source, wherein about 11% to about 99% of unsaturated fatty acids in the biological oil are polyunsaturated fatty acids. In some embodiments of the present invention, greater than about 50% of unsaturated fatty acids in the biological oil are polyunsaturated fatty acids.

The microorganism used in the present invention can be, but is not limited to, a Thraustochytrid, preferably selected from the group consisting of microorganisms of the genus *Schizochytrium*, microorganism of the genus *Thraustochytrium*, and microorganisms of the genus *Ulkenia*.

In some embodiments of the present invention, the microorganism used saccharifies the cellulose. Preferably, a microorganism of the present invention degrades or is resistant to feedstock components selected from the group consisting of lignin, hemicellulose, plant oil, plant extracellular polysaccharides, and combinations thereof. In some embodiments of the present invention, the microorganism is a genetically modified microorganism.

A microorganism of the present invention can produce oil in triglyceride form in an amount of from about 25% to about 85% by weight of its dry biomass. In some embodiments of the present invention, the growing of the microorganism biomass is performed at a dissolved oxygen concentration of from about 10% to about 100%. The production of biological oil by the microorganism may be performed at a dissolved oxygen concentration of, for example, from 0% to about 10%. The microorganisms can grow at a temperature of from about 15° C. to about 45° C.

In some embodiments of the present invention, the method of producing biological oil further comprises performing autolysis or induced lysis of the microorganism after the microorganism has produced oil in an amount of from about 30% to about 90% by weight of its dry biomass. Inducing lysis of the microorganism may be achieved by exposing the microorganism to a condition favorable for lysis selected from the group consisting of a pH, a temperature, the presence of an enzyme, the presence of a detergent, physical disruption, and combinations thereof.

In some embodiments of the present invention, the fermentation feedstock containing cellulose comprises a source of cellulose selected from the group consisting of grass, sugar cane, agricultural waste, waste paper, sewage, wood, an organism of the kingdom viridiplantae, and combinations thereof.

In preferred embodiments of the present invention, the fermentation is performed in a nonsterile fermentor. In some embodiments of the invention, the fermentation is performed in a fermentor selected from the group consisting of fiber reinforced polymer fermentors, metal matrix composite fermentors, ceramic matrix composite fermentors, thermoplastic composite fermentors, metal fermentors, epoxy lined carbon steel fermentors, plastic lined carbon steel fermentors, plastic fermentors, fiberglass fermentors, and concrete fermentors.

In some embodiments of the present invention, the fermentation is carried out in a fermentor that is submerged in water. The fermentation can be carried out in fermentors having cooling systems connected in series such that cooling water effluent from a first fermentor or a set of fermentors in the series is used as a cooling water supply for a second fermentor or set of fermentors in the series. Similarly, the fermentation can be carried out in fermentors having gas systems connected in series such that sparge exhaust from a first fermentor or a set of fermentors in the series is used as a gas supply for a second fermentor or set of fermentors in the series.

The present invention further provides a method for producing biodiesel comprising (a) growing a microorganism of the kingdom Stramenopile by heterotrophic fermentation using feedstock comprising cellulose as a carbon source to produce a biological oil, wherein about 11% to about 99% of unsaturated fatty acids in the biological oil are polyunsaturated fatty acids; and (b) transesterifying the biological oil to produce biodiesel. In some embodiments of the present invention, greater than about 50% of unsaturated fatty acids in the biological oil are polyunsaturated fatty acids.

The transesterifying of the biological oil may be performed using an alcohol derived from an alcohol production process. In some embodiments of the present invention, glycerol resulting from the transesterifying of the biological oil can be used as a carbon source for a subsequent fermentation process to produce an alcohol or a biological oil. In some embodiments of the present invention, a subsequent fermentation process grows a microorganism that is capable of using the glycerol as a carbon source.

The present invention also provides a method for producing jet biofuel comprising (a) growing a microorganism of the kingdom Stramenopile by heterotrophic fermentation using feedstock comprising cellulose as a carbon source to produce a biological oil, wherein about 11% to about 99% of unsaturated fatty acids in the biological oil are polyunsaturated fatty acids; and (b) cracking the biological oil to produce jet biofuel. In some embodiments of the present invention, the biological oil used to produce jet biofuel comprises about 10% to about 75% by weight of polyunsaturated fatty acids.

The present invention provides a lipid-based biofuel composition comprising from about 1% to about 75% by weight of alkyl esters of long chain fatty acids having 20 or more carbons. In some embodiments of the present invention, the lipid-based biofuel composition has a melting temperature of from about 30° C. to about −50° C.

The present invention also provides a method for producing a biological oil comprising: (a) growing two or more microorganisms simultaneously or sequentially by heterotrophic fermentation, using feedstock comprising cellulose as a carbon source, wherein one or more of the microorganisms are capable of saccharifying said cellulose.

The present invention further provides a method for producing biodiesel comprising transesterifying a biological oil produced by two or more microorganisms that have undergone heterotrophic fermentation using feedstock comprising cellulose as a carbon source, wherein one or more of the microorganisms are capable of saccharifying the cellulose. To produce jet biofuel, cracking may be performed on a biological oil produced by two or more microorganisms that have undergone heterotrophic fermentation using feedstock comprising cellulose as a carbon source, wherein one or more of the microorganisms are capable of saccharifying the cellulose.

The present invention provides a method of producing a biological oil comprising growing a microorganism by heterotrophic fermentation in a nonsterile fermentor. In some embodiments of the present invention, the biological oil is produced at a rate of about 5 g/L/day to about 70 g/L/day, preferably at a rate of about 30 g/L/day to about 70 g/L/day in the nonsterile fermentor.

In some embodiments of the present invention, growing the microorganisms in the nonsterile fermentor achieves a cell density of about 10 g/L to about 300 g/L, preferably about 150 g/L to about 250 g/L. Preferably, the growing of the microorganism comprises using cellulose as a carbon source.

The present invention also provides a method of producing biodiesel comprising: (a) growing a microorganism in a nonsterile fermentor to produce a biological oil; and (b) transesterifying the biological oil to produce biodiesel. The present invention further provides a method of producing jet biofuel comprising: (a) growing a microorganism in a nonsterile fermentor to produce a biological oil; and (b) cracking the biological oil to produce jet biofuel.

The present invention provides a method of producing biodiesel comprising: (a) growing a microorganism using nutrients comprising recycled media to produce a biological oil; and (b) transesterifying the biological oil to produce biodiesel. The recycled media can be, but is not limited to, de-lipidated biomass, hydrolyzed biomass, partially hydrolyzed biomass, recycled metals, recycled salts, recycled amino acids, recycled extracellular carbohydrates, recycled glycerol, recycled yeast biomass, and combinations thereof. Preferably, growing the microorganism comprises using cellulose as a carbon source.

The present invention further provides a method of producing jet biofuel comprising: (a) growing a microorganism using nutrients comprising recycled media to produce a biological oil; and (b) cracking the biological oil to produce jet biofuel.

Some embodiments of the present invention provide a method of producing biodiesel comprising: (a) growing a microorganism using a fermentation system comprising a continuous seed stage and a lipid-production stage to produce a biological oil; and (b) transesterifying the biological oil to produce biodiesel. Preferably, the continuous seed stage produces biomass of the microorganism such that about 10% to about 95% of the total biomass production of the microorganism is achieved during the continuous seed stage. In some embodiments of the present invention, the lipid-production stage is carried out as a fed-batch process. Preferably, the lipid-production stage produces lipids such that about 10% to about 95% of the total lipid production of the microorganism is achieved during the lipid-production stage. In some embodiments of the present invention, growing the microorganism comprises using cellulose as a carbon source.

The present invention further provides a method of producing jet biofuel comprising: (a) growing a microorganism using a fermentation system comprising a continuous seed stage and a lipid-production stage to produce a biological oil; and (b) cracking the biological oil to produce jet biofuel.

DETAILED DESCRIPTION OF THE INVENTION

Figure 1:
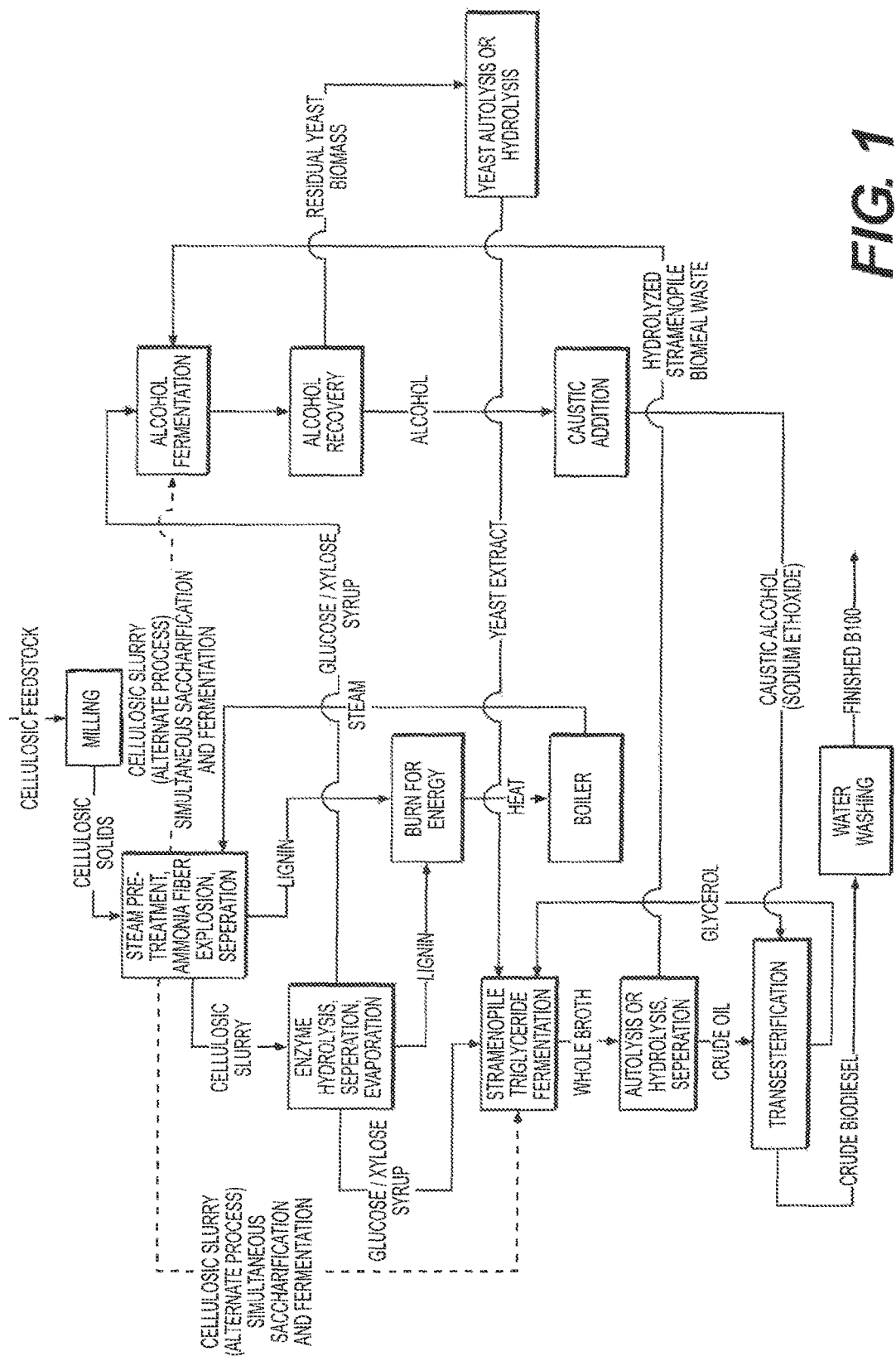
FIG. 1 shows various embodiments of a method of producing biological oils and biodiesel in accordance with the present invention.
Figure 2:
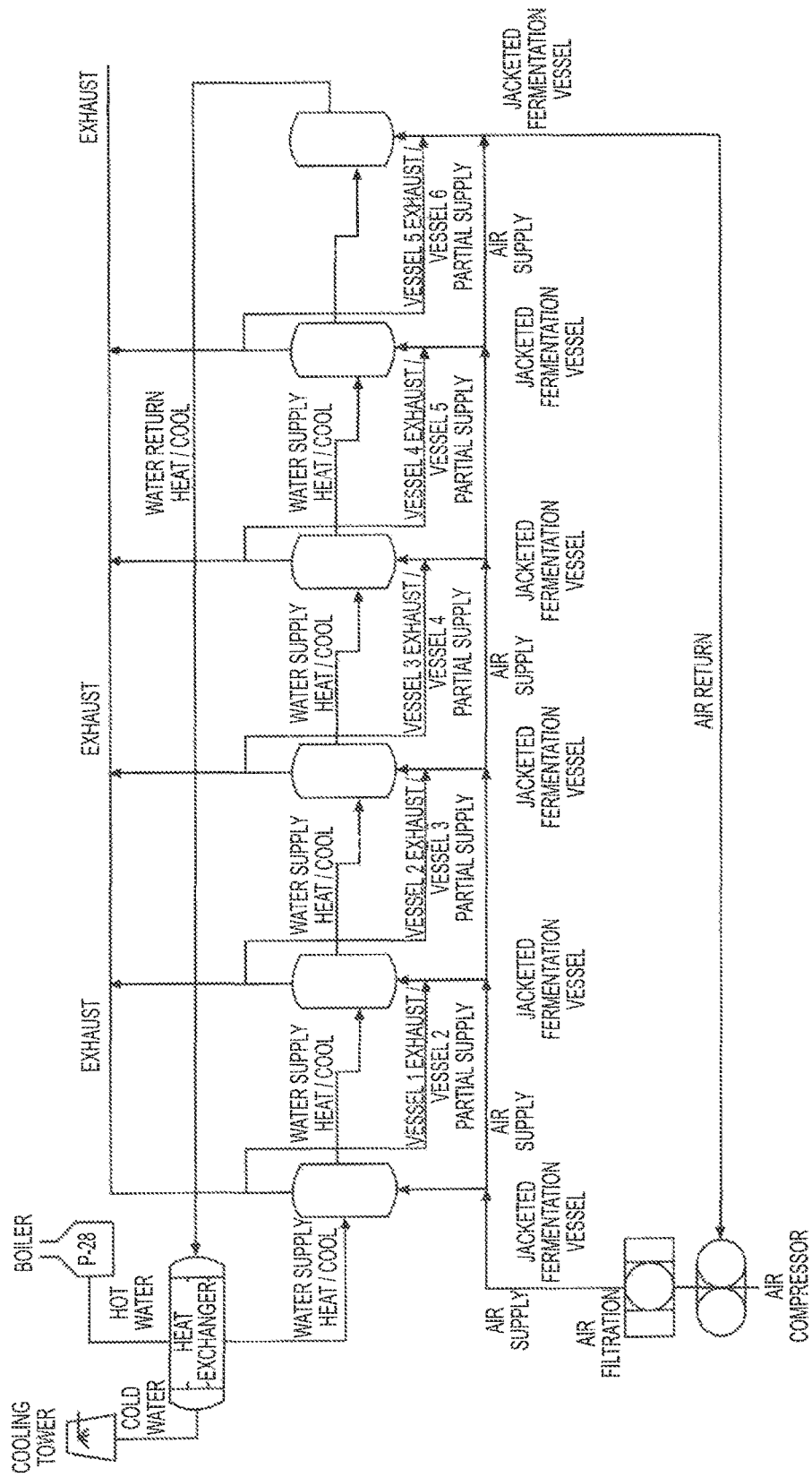
FIG. 2 shows an example of a fermentation system design in accordance with the present invention.

The present invention provides biological oils and uses and production thereof. Some embodiments of the present invention provide oleaginous, heterotrophic organisms and processes suitable for converting carbon, via fermentation, from directly cellulose-based or ligno-cellulose based saccharides into vegetable oil for biodiesel manufacturing. The processes of the present invention would be more scalable, sustainable, and would generate a more cost-competitive biodiesel than currently used or researched processes (such as seed-oil biodiesel or photosynthetic algal biodiesel).

Some aspects of the present invention involve high density growth of two, oleaginous microorganisms using saccharified cellulosic feedstocks. For example, the protist *Schizochytrium* sp. and the oleaginous yeast *Yarrowia lipolytica* are suitable for such processes because both have well-developed transformation systems for modifying the microorganisms and are capable of producing high levels of lipid by fermentation. Some aspects of the present invention provide oleaginous thraustochytrids and fungi capable of growing on a variety of cellulosic and ligno-cellulosic substrates, and organisms that may be naturally amenable to combined saccharification and fermentation, as well as lignin degradation or resistance.

The present invention is also directed to improved strains of organisms and processes for utilizing cellulose-based substrates for oil production via molecular, biological, classical genetic, and physiological means. Some embodiments of the present invention provide an economical scale-up of a fermentation process for converting cellular acylglycerides into biodiesel. The present invention also provides biological and chemical reactor designs and constructions, as well as commercial production strategies for the implementation of the methods of the invention.

Various organisms can be used for the production of biological oil in accordance with the present invention, including microorganisms. The microorganisms can be algae, bacteria, fungi or protists. Microbial sources and methods for growing microorganisms are known in the art (Industrial Microbiology and Biotechnology, 2nd edition, 1999, American Society for Microbiology). For example, the microorganisms can be cultured in a fermentation medium in a fermentor. Oils produced by microorganisms can be used in the methods and compositions of the present invention. In some embodiments, organisms include those selected from the group consisting of golden algae (such as microorganisms of the kingdom Stramenopiles), green algae, diatoms, dinoflagellates (such as microorganisms of the order Dinophyceae including members of the genus *Crypthecodinium* such as, for example, *Crypthecodinium cohnii*), yeast (such as a member of the genera *Yarrowia* (such as *Yarrowia lipolytica*), *Cryptococcus* (such as *Cryptooccus albidus*), *Trichosporon*, *Candida*, *Lipomyces*, *Rhodosporidium*, and *Rhodotorula*), and fungi of the genera *Mucor* and *Mortierella*, including but not limited to *Mortierella alpina* and *Mortierella* sect. *schmuckeri*. Members of the microbial group Stramenopiles include microalgae and algae-like microorganisms, including the following groups of microorganisms: Hamatores, Proteromonads, Opalines, Develpayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinaales, Pedinellales, Dictyochales), Chrysomeridales, Sarcinochrysidales, Hydrurales, Hibberdiales, and Chromulinales. The Thraustochytrids include the genera *Schizochytrium* (species include *aggregatum, limnaceum, mangrovei, minutum, octosporum*), *Thraustochytrium* (species include *arudimentale, aureum, benthicola, globosum, kinnei, motivum, multirudimentale, pachydermum, proliferum, roseum, striatum*), *Ulkenia* (species include *amoeboidea, kerguelensis, minuta, profunda, radiate, sailens, sarkariana, schizochytrops, visurgensis, yorkensis*), *Aplanochytrium* (species include *haliotidis, kerguelensis, profinda, stocchinoi*), *Japonochytrium* (species include *marinum*), *Althornia* (species include *crouchii*), and *Elina* (species include *marisalba, sinorifica*). The Labrinthulids include the genera *Labyrinthula* (species include *algeriensis, coenocystis, chattonii, macrocystis, macrocystis atlantica, macrocystis macrocystis, marina, minuta, roscoffensis, valkanovii, vitellina, vitellina pacifica, vitellina vitellina, zopfi*), *Labyrinthomyxa* (species include marina), *Labyrinthuloides* (species include *haliotidis, yorkensis*), Diplophrys (species include *archeri*), Pyrrhosorus* (species include *marinus*), Sorodiplophrys* (species include *stercorea*), Chlamydomyxa* (species include *labyrinthuloides, montana*). (*=there is no current general consensus on the exact taxonomic placement of these genera).

Some embodiments of the present invention provide a method for producing a biological oil comprising growing a microorganism of the kingdom Stramenopile by heterotrophic fermentation using feedstock comprising cellulose as a carbon source. In some embodiments of present invention, the biological oil contains unsaturated fatty acids of which a significant portion is polyunsaturated fatty acids. As described previously, certain polyunsaturated fatty acids such as omega-3 and omega-6 long chain polyunsaturated fatty acids are particularly important dietary compounds. Therefore, it is desirable to produce a biological oil with a significant amount of polyunsaturated fatty acids. In some embodiments of the present invention, the biological oils are converted to lipid-based biofuels. For such applications, it may be desirable to produce hydrocarbons of various chain lengths, particularly for jet biofuel applications. The presence of significant amounts of polyunsaturated fatty acids in the biological oils used to produce lipid-based biofuels will provide greater flexibility and variety for the production of hydrocarbons since the multiple sites of unsaturation in a polyunsaturated fatty acid provide multiple sites for cleavage to make hydrocarbons. For example, certain jet fuels require hydrocarbons with two to eight carbons. The polyunsaturated fatty acids may be cleaved through known processes in the art, such as cracking, to produce shorter hydrocarbons of various chain lengths.

In some embodiments, the biological oils produced through the methods of the present invention has unsaturated fatty acids wherein about 11% to about 99% of the unsaturated fatty acids in the biological oil are polyunsaturated fatty acids. The biological oils of the present invention may contain unsaturated fatty acids wherein about 20% to about 99%, about 26% to about 99%, about 30% to about 99%, about 40% to about 99%, about 51% to about 99%, about 60% to about 99%, about 70% to about 99%, about 80% to about 99%, or about 90% to about 99% of the unsaturated fatty acids in the biological oil are polyunsaturated fatty acids. In some embodiments of the present invention, greater than about 10%, greater than about 20%, greater than about 25%, greater than about 30%, greater than about 40%, greater than about 50%, greater than about 60%, greater than about 70%, greater than about 80%, or greater than about 90% of the unsaturated fatty acids in the biological oil are polyunsaturated fatty acids.

In some embodiments of the present invention, the biological oil comprises about 10% to about 75% by weight of polyunsaturated fatty acids. For certain uses, the biological oil preferably comprises about 20% to about 75%, about 30% to about 75%, about 40% to about 75%, about 50% to about 75%, or about 60% to about 75% by weight of polyunsaturated fatty acids. In some embodiments of the present invention, the biological oil comprises at least about 10%, at least about 200%, at least about 30%, at least about 40%0, at least about 50%, at least about 60%, or at least about 70% by weight of polyunsaturated fatty acids. The methods of producing a biological oil in accordance with the present invention may optionally further comprise collecting the biological oil from the microorganism.

As used herein, "cellulose" includes unsaccharified or unhydrolyzed cellulose, as well as saccharified or hydrolyzed cellulose. In some embodiments of the present invention, the microorganism used is a Thraustochytrid. Preferably, the microorganism is of the genus *Schizochytrium*, *Thraustochytrium*, or *Ulkenia*. In some embodiments of the present invention, the microorganism used is a yeast of the genus *Yarrowia* (such as *Yarrowia lipolytica*), *Cryptococcus* (such as *Cryptococcus albidus*), *Trichosporon*, *Candida*, *Lipomyces*, *Rhodosporidium*, or *Rhodotorula*. Patent application publication no. WO 2004/101757, the contents of which are incorporated herein by reference in its entirety, discloses examples of these yeasts.

The present invention further contemplates the use of a combination of two or more microorganisms for producing a biological oil or a blend of biological oils. To reduce the costs of fermentation, two or more microorganisms are preferably grown under the same fermentation conditions. When two or more different microorganisms are combined to produce the biological oil, one or more microorganisms may accumulate oil during fermentation. One or more microorganisms may facilitate the growth and accumulation of oil by another microorganism through activity such as, but not limited to, the breakdown of feedstock components into usable sugar monomers (such as the saccharification of cellulose), the breakdown of feedstock components that inhibit growth of another microorganism (such as metabolizing or degrading feedstock components such as lignin, hemicellulose (such as xylan, glucuronoxylan, arabinoxylan, glucomannan, and xyloglucan), plant oils, plant extracellular polysaccharides, etc.), and the synthesis of components that promote growth of another microorganism (such as through synthesis of certain enzymes that facilitate growth of the microorganism).

Organisms suitable for the metabolization of hemicellulose include, but are not limited to, *Fibrobacter succinogenes*, and yeasts of the genera *Cryptococcus* (such as *Cryptococcus albidus, Cryptococcus curvatus*), *Trichosporon, Candida, Lipomyces, Rhodosporidium*, and *Rhodotorula*. Other organisms suitable for metabolization of hemicellulose include species of *Pichia* (such as *Pichia stipitis*), *Aeromonas, Aspergillus, Streptomyces, Rhodococcus, Bacillus* (such as *Bacillus subtilis, Bacillus brevis*, and *Bacillus*

*lentis*), *Echerichia*, *Kluyveromyces*, *Saccharomyces* and organisms of the genera *Trichoderma*, Organisms suitable for the metabolization of lignin include, but are not limited to, *Phanerochaete chrysosporium* and other "white rot" fungi. Patent application publication no. WO 91/018974, the contents of which are incorporated herein by reference in its entirety, discloses examples of organisms that have hemicellulase activity.

Methods suitable for use in the present invention for generating free sugars and oligosaccharides from lignocellulosic biomass are disclosed, for example, in patent application publication no. US 2004/0005674, the content of which is incorporated herein by reference in its entirety. These methods involve converting lignocellulosic biomass to free sugars and small oligosaccharides with enzymes (such as cellulases, xylanases, ligninases, amylases, proteases, lipidases and glucuronidases) that break down lignocellulose. These enzymes may be bought from a commercial source or produced recombinantly, such as by expression either in microorganisms, fungi, i.e., yeast, or plants.

Oleaginous microorganisms are preferred for use in the present invention. As used herein, "oleaginous microorganisms" are defined as microorganisms capable of accumulating greater than 20% of the dry weight of their cells in the form of lipids. In some embodiments of the present invention, a microorganism produces from about 30% to about 95% by weight of its dry biomass as lipids. Preferably, a microorganism of the present invention produces from about 35% to about 93%, from about 40% to about 90%, from about 45% to about 88%, from about 50% to about 85%, from about 55% to about 83%, from about 60% to about 80%, from about 65% to about 78%, or from about 70% to about 75% by weight of its dry biomass as lipids. In some embodiments of the present invention, the microorganism produces at least about 30%, at least about 35%, at least about 40%, at least about 45%, at least about 50%, at least about 55%, at least about 60%, at least about 65%, or at least about 70% by weight of its dry biomass as lipids.

When two or more microorganisms are used to produce the biological oils of the present invention, one or more microorganisms may produce biological oils. In some embodiments of the present invention, when two or more microorganisms are combined to produce biological oils, the ratio of the amount of oil produced by a first microorganism to the amount of oil produced by a second microorganism, as measured by weight, is from about 1:9 to about 1:1, from about 1:9 to about 2:3, from about 1:9 to about 3:7, or from about 1:9 to about 1:4.

Preferably, a microorganism of the present invention produces oil in triglyceride form in an amount of from about 25% to about 85% by weight of its dry biomass, from about 30% to about 85% by weight of its dry biomass, from about 35% to about 85% by weight of its dry biomass, from about 40% to about 85% by weight of its dry biomass, from about 45% to about 85% by weight of its dry biomass, from about 50% to about 85% by weight of its dry biomass, from about 55% to about 85% by weight of its dry biomass, from about 60% to about 85% by weight of its dry biomass, from about 60% to about 80% by weight of its dry biomass, from about 65% to about 80% by weight of its dry biomass, from about 65% to about 75% by weight of its dry biomass, or from about 70% to about 75% by weight of its dry biomass. In some embodiments of the present invention, the microorganism produces oil in triglyceride form in an amount of at least about 25%, at least about 30%, at least about 35%, at least about 40%, at least about 45%, at least about 50%/a, at least about 55%, at least about 60%, at least about 65%, or at least about 70% by weight of its dry biomass.

As used herein, a "triglyceride" is an ester of three fatty acid residues and glycerol having a general chemical formula of $CH_2(OOCR^1)CH(OOCR^2)CH_2(OOCR^3)$, wherein each of $OOCR^1$, $OOCR^2$, and $OOCR^3$ represents a fatty acid residue. In some embodiments of the present invention, suitable triglycerides may contain at least one PUFA. In some embodiments, the PUFA has a chain length of at least 18 carbons. Such PUFAs are referred to herein as long chain PUFAs or LC PUFAs. In some embodiments, the PUFA can be docosahexaenoic acid C22:6 n-3 (DHA), omega-3 docosapentaenoic acid C22:5 n-3 (DPA(n-3)), omega-6 docosapentaenoic acid C22:5 n-6 (DPA(n-6)), arachidonic acid C20:4 n-6 (ARA), eicosapentaennoic acid C20:5 n-3 (EPA), stearidonic acid (SDA), linolenic acid (LLA), alpha linolenic acid (ALA), gamma linolenic acid (GLA), conjugated linolenic acid (CLA), eicosatetraenoic acid (C20:4 n-3), homo-alpha and -gamma linolenic acid (C20:3 n-6 and 20:3 n-3), adrenic acid (C22:4 n-6), octacosaoctaenoic acid (C28:8), or mixtures thereof. The PUFAs can also be present in any of the common forms found in natural lipids including but not limited to triacylglycerols, diacylglycerols, monoacylglycerols, phospholipids, free fatty acids, or in natural or synthetic derivative forms of these fatty acids (e.g. calcium salts of fatty acids, and the like). Reference to an oil or other composition comprising triglycerides having PUFA residues, as used in the present invention, can refer to either a composition comprising triglycerides having only a single type of PUFA residue such as DHA or a composition comprising triglycerides having a mixture of more than one type of PUFA residues such as DHA, EPA and ARA.

In preferred embodiments of the present invention, the microorganisms are capable of high density cell growth. In some embodiments of the present invention, the microorganisms are capable of achieving a cell density of at least about 10 g/L, at least about 15 g/L, at least about 20 g/L, at least about 25 g/L, at least about 30 g/L, at least about 50 g/L, at least about 75 g/L, at least about 100 g/L, at least about 125 g/L, at least about 135 g/L, at least about 140 g/L, at least about 145 g/L, or at least about 150 g/L. In some embodiments of the present invention, the microorganisms are capable of achieving a cell density of from about 10 g/L to about 300 g/L, from about 15 g/L to about 300 g/L, from about 20 g/L to about 300 g/L, from about 25 g/L to about 300 g/L, from about 30 g/L to about 300 g/L, from about 50 g/L to about 300 g/L, from about 75 g/L to about 300 g/L, from about 100 g/L to about 300 g/L, from about 125 g/L to about 300 g/L, from about 130 g/L to about 290 g/L, from about 135 g/L to about 280 g/L, from about 140 g/L to about 270 g/L, from about 145 g/L to about 260 g/L, or from about 150 g/L to about 250 g/L. The high density growth of the microorganisms of the present invention can be increased by adjusting the fermentation conditions (such as temperature, pH, concentration of ions, and gas concentrations).

The present invention provides highly efficient production of the biological oils. In some embodiments of the present invention, the amount of biological oil produced is at least about 5 g/L/day, at least about 10 g/L/day, at least about 20 g/L/day, at least about 30 g/L/day, at least about 40 g/L/day, at least about 50 g/L/day, at least about 60 g/L/day, or at least about 70 g/L/day. In some embodiments of the present invention, the amount of biological oil produced is from about 5 g/L/day to about 70 g/L/day, from about 10 g/L/day to about 70 g/L/day, from about 20 g/L/day to about 70 g/L/day, or from about 30 g/L/day to about 70 g/L/day.

In some embodiments of the present invention, the microorganism used for the production of the biological oil is a cellulolytic microorganism and therefore is capable of saccharifying cellulose from cellulosic or ligno-cellulosic feedstocks. Cellulosic or ligno-cellulosic feedstocks include any sources comprising cellulose. These include, but are not limited to, grasses, sugar cane, agricultural waste, waste paper, sewage, wood, and any organism in the viridiplantae kingdom or products thereof. Preferably, the cellulose used is from a source other than tree-based cellulose sources. The types of grasses useful as a source of cellulose include, but are not limited to, saw grass, wheat grass, rice grass, switch grasses, and *Miscanthus* type grasses.

In order for a microorganism to use cellulose as a carbon source, the cellulose must be broken down to its constituent sugar monomers. Cellulose is a polymer of glucose linked by beta-glucoside bonds which provide a highly stable linear structure. The breakdown of cellulose into sugar monomers (also referred to as saccharifying the cellulose) is a difficult challenge and many attempts have been made to accomplish this. Enzymatic hydrolysis of cellulose by cellulases is one approach to degrade cellulose. A complete hydrolysis of cellulose generally requires: an endoglucanase, which cleaves interior regions of cellulose polymers; an exoglucanase, which cleaves cellobiose units from the ends of cellulose polymers; and a beta-glucosidase, which cleaves cellobiose into its glucose subunits. Cellulases may have multiple complexes that accomplish the activities of an endoglucanase, an exoglucanase, and a beta-glucosidase. *Trichoderma reesei* is an important organism used for the production of cellulases. Other methods of breaking down cellulose into sugar monomers include thermochemical disruptions (with or without mechanical disruptions), including hot water, steam explosion, acid treatments, and/or ammonia fiber explosion.

In some embodiments of the present invention, the microorganism that is grown to produce the biological oil is the same microorganism that saccharifies the cellulose. In some embodiments of the present invention, two or more microorganisms can be grown, either simultaneously or sequentially, to produce biological oils using cellulose-containing feedstock as a main carbon source. In accordance with the present invention, when two or more microorganisms are fermented simultaneously or sequentially, one or more of the microorganisms are capable of saccharifying cellulose. In some embodiments of the present invention, a microorganism can undergo heterotrophic fermentation in the presence of a cellulase to enhance the saccharification of cellulose during fermentation. In some embodiments, at least one of the microorganisms is from the Stramenopile kingdom, and preferably is a member of the group commonly called thraustochytrids.

The microorganisms suitable for use in the present invention may also be tolerant of high temperatures and/or highly acidic or basic environments such that their growth is not inhibited and, in some cases, is even enhanced by high temperatures and/or acidic mediums. In some embodiments of the present invention, a microorganism is grown by heterotrophic fermentation using cellulose-containing feedstock at a temperature and/or a pH that facilitates the degradation of cellulose. In some embodiments of the present invention, the fermentation is performed at a temperature of from about 15° C. to about 70° C., from about 20° C. to about 40° C., or from about 25° C. to about 35° C. In further embodiments of the present invention, the fermentation is performed at a pH of from about 3 to about 11, from about 3 to about 10, from about 4 to about 9.5, from about 4 to about 9, from about 5 to about 7, or from about 6 to about 9. Pretreatment of cellulose-containing feedstocks using, for example, cellulases, chemical and/or mechanical disruptions, and ammonia fiber explosions can also be performed prior to using the feedstocks in the production of the biological oils of the present invention. Alternatively, no such pretreatment is necessary.

Some examples of methods of pretreating feedstock are disclosed in patent application publication nos. US 2007/0161095, WO 05/053812, WO 06/086757, US 2006/0182857, US 2006/177551, US 2007/0110862, WO 06/096834, WO 07/055735, US 2007/0099278, WO 06/119318, US 2006/0172405, and US 2005/0026262, the contents of which are incorporated herein by reference in their entirety.

Examples of enzymes suitable for digestion of cellulose are disclosed in patent or patent application publication nos. US 2003/0096342, WO 03/012109, U.S. Pat. No. 7,059,993, WO 03/012095, WO 03/012090, US 2003/0108988, US 2004/0038334, US 2003/0104522, EP 1 612 267, and WO 06/003175, the contents of which are incorporated herein by reference in their entirety.

In some embodiments of the present invention, the cellulosic feedstock that is used to grow a microorganism comprises cellulose in an amount of from about 5% to about 100%, from about 10% to about 95%, from about 20% to about 90%, from about 30% to about 85%, from about 40% to about 80%, from about 50% to about 75%, or from about 60% to about 70% by dry weight of the carbon feedstock. In some embodiments of the present invention, the cellulosic feedstock comprises cellulose in an amount of at least about 5%, at least about 10%, at least about 20%, at least about 30%, at least about 40%, at least about 50%, at least about 60%, or at least about 70% of the dry weight of the carbon feedstock.

Preferably, the microorganism used in the present invention is resistant to or degrades feedstock components such as lignin, xylan, hemicellulose, plant oil, plant extracellular polysaccharides, and combinations thereof. The degradation of or resistance to these feedstock components ensures that the fermentation performance of the microorganism will not be inhibited by the presence of these components.

In some embodiments of the present invention, the cellulosic feedstock used to grow a microorganism comprises from about 1% to about 50%, from about 5% to about 40%, or from about 10% to about 30% by weight of a component selected from lignin, hemicellulose, or a combination thereof. In some embodiments of the present invention, the cellulosic feedstock used to grow a microorganism comprises at least about 1%, at least about 5%, at least about 10%, at least about 20%, or at least about 30% by weight of a component selected from lignin, hemicellulose, or a combination thereof.

Suitable organisms can be obtained from a number of available sources, including by collection from the natural environment. As used herein, any organism, or any specific type of organism, includes wild strains, mutants, or recombinant types. Growth conditions in which to culture or grow these organisms are known in the art, and appropriate growth conditions for at least some of these organisms are disclosed in, for example, U.S. Pat. No. 5,130,242, U.S. Pat. No. 5,407,957, U.S. Pat. No. 5,397,591, U.S. Pat. No. 5,492,938, U.S. Pat. No. 5,711,983 and U.S. Pat. No. 6,607,900, all of which are incorporated herein by reference in their entirety. When microbial oils are used, the microorganisms are cultured in an effective medium, herein defined as any medium capable of promoting oil production.

Preferably, the effective medium also promotes rapid microbial growth. The microorganisms can be cultured in conventional fermentation modes, which include, but are not limited to, batch, fed-batch, semi-continuous, and continuous. As used herein, a "semi-continuous" mode refers to a mode of fermentation in which a portion of the fermentation culture containing microorganisms is not harvested from the fermentor after the completion of a fermentation process. The portion of the fermentation culture remaining in the fermentor can serve to inoculate a subsequent fermentation process. In some embodiments of the present invention, from about 1% to about 50%, from about 1% to about 25%, from about 1% to about 15%, from about 1% to about 10%, or from about 2% to about 8% by volume of the fermentation culture is not harvested after completion of the fermentation process, and is allowed to remain in the fermentor to inoculate a subsequent fermentation process.

In some embodiments of the present invention, the fermentation process comprises a first stage that targets accumulation of biomass of the microorganism and a second stage that targets lipid accumulation by the microorganism. Preferably, there is no nutrient limitation during the biomass accumulation stage. The lipid accumulation stage is preferably carried out with nitrogen limitation with a carbon feed.

The methods of the present invention for producing biodiesel can comprise (a) growing a microorganism using a fermentation system comprising a continuous seed stage and a lipid-production stage to produce a biological oil, and (b) converting the biological oil into biodiesel through known means in the art, such as through transesterifying the biological oil to produce biodiesel. The continuous seed stage targets biomass accumulation and is performed by providing continuous nutrient feed to the seed vessel (the vessel with the initial inoculation). The fermentation broth from the seed vessel is withdrawn and transferred to a lipid-production stage vessel, which may run as a fed-batch process where a carbon source is fed to the batch to maintain a target sugar concentration throughout the run.

A similar two-stage fermentation process can be used to produce biological oil for the production of jet biofuel. In some embodiments of the present invention, the methods of producing jet biofuel comprises converting the biological oil produced using this fermentation system into jet biofuel by methods known in the art, utilizing processes such as cracking to assist in transforming the biological oil into a jet biofuel.

The two-stage fermentation process increases the efficiency of the biological oil production process and therefore contributes to lowering the cost of lipid-based biofuel production. This improved fermentation system for the production of lipid-based biofuel is particularly advantageous in maximizing efficient, large-scale production of biological oils and therefore makes a significant contribution to making lipid-based biofuel production from biological oils more commercially feasible. The two-stage fermentation process may be used to produce biological oil with high or low polyunsaturated fatty acid content, depending on the requirements of a specific application.

In some embodiments of the present invention, the biomass accumulation stage (such as the continuous seed stage) produces biomass of the microorganism such that about 10% to about 95%, about 20% to about 95%, about 30% to about 95%, about 40% to about 95%, or about 50% to about 95% of the total biomass production of the microorganism is achieved during the biomass accumulation stage. In further embodiments of the present invention, about 60% to about 95%, about 70% to about 95%, or about 80% to about 95% of the total biomass production of the microorganism is achieved during the biomass accumulation stage. In some embodiments of the present invention, the biomass accumulation stage produces biomass of the microorganism such that at least about 10%, at least about 20%, at least about 30%, at least about 40%, at least about 50%, at least about 60%, at least about 70%, at least about 80%, at least about 90%, or at least about 95% of the total biomass production of the microorganism is achieved during the biomass accumulation stage. Preferably, about 50% to about 95% of the total biomass production of the microorganism is achieved during the biomass accumulation stage.

In some embodiments of the present invention, the lipid accumulation stage produces lipids such that about 10% to about 95%, about 20% to about 95%, about 30% to about 95%, about 40% to about 95%, or about 50% to about 95% of the total lipid production of the microorganism is achieved during the lipid accumulation stage. In further embodiments of the present invention, about 60% to about 95%, about 70% to about 95%, or about 80% to about 95% of the total lipid production of the microorganism is achieved during the lipid accumulation stage. In some embodiments of the present invention, the lipid accumulation stage produces lipids such that at least about 10%, at least about 20%, at least about 30%, at least about 40%, at least about 50%, at least about 60%, at least about 70%, at least about 80%, at least about 90%, or at least about 95% of the total lipid production of the microorganism is achieved during the lipid accumulation stage. Preferably, about 50% to about 95% of the total lipid production of the microorganism is achieved during the lipid accumulation stage.

Genetically modified microorganisms are also suitable for the present invention. Microorganisms of the present invention may be genetically modified to enhance their ability to produce biological oils at reduced costs (for example, through an enhanced ability to use cellulose-based feedstock as a main carbon source). These genetically modified microorganism can include, but are not limited to, microorganisms that have been genetically modified to have an enhanced ability to saccharify cellulose or cellulosic feedstock, to have increased oil production, to have the ability to degrade lignin or be resistant to lignin, or to grow in culture conditions that are not optimal for the corresponding wild-type organism (such as high temperatures or highly acidic mediums). For example, a microorganism can be genetically modified to introduce or enhance the activities of an endoglucanase, an exoglucanase, and/or a beta-glucosidase.

Genes from organisms used to develop cellulases can be introduced into a microorganism to enhance its ability to saccharify cellulose. For example, genes encoding components of cellulases from organisms of the genera *Trichoderma, Clostridium, Cellulomonas, Thermobifida, Acidothermus, Schizochytrium*, or *Thraustochytrium* can be introduced into a microorganism of the present invention through recombinant genetic techniques to produce a microorganism that is capable of directly saccharifying cellulose. Preferably, genes encoding cellulase components from the species *Trichoderma reesei, Clostridium thermocellum, Acidothermus cellulolyticus*, or *Schizochytrium aggregatum* are introduced and expressed in microorganisms of the present invention. In some embodiments of the present invention, a cellulase from one organism is cloned into a different organism.

Genetic transformation techniques for microorganisms are well-known in the art and are discussed, for example, in Sambrook et al., 1989, *Molecular Cloning: A Laboratory*

*Manual*, Cold Spring Harbor Labs Press. A general technique for transformation of dinoflagellates, which can be adapted for use with *Crypthecodinium cohnii*, is described in detail in Lohuis and Miller, *The Plant Journal* (1998) 13(3): 427-435. A general technique for genetic transformation of Thraustochytrids is described in detail in U.S. Patent Application Publication No. 20030166207, published Sep. 4, 2003.

In some embodiments of the present invention, fermentation of the microorganisms to produce biological oils is performed under low dissolved oxygen concentrations. The ability of the microorganisms to grow and produce oil at low dissolved oxygen concentrations reduces energy input into fermentation, and therefore would also reduce the cost of fermentation. In some embodiments of the present invention, the growing of the microorganism biomass (biomass accumulation stage) is performed at a dissolved oxygen concentration of from about 4% to about 100%, from about 10% to about 100%, from about 10% to about 80%, from about 10% to about 70%, from about 10% to about 60%, from about 15% to about 50%, or from about 20% to about 40%. The production of biological oil by the microorganism (the lipid accumulation stage) may be performed at a dissolved oxygen concentration of, for example, from 0% to about 10%, from 0% to about 8%, from about 1% to about 5%, or from about 1% to about 3%.

To reduce energy costs associated with the cooling of the fermentors, the microorganisms used in the present invention are preferably temperature tolerant over a wide range of temperatures. In some embodiments of the present invention, the microorganisms can grow and produce oil at a temperature of from about 15° C. to about 45° C., from about 20° C. to about 45° C., from about 25° C. to about 45° C., from about 30° C. to about 45° C., or from about 35° C. to about 45° C.

Conventionally, the fermentation of a microorganism is usually carried out in a sterile environment to avoid contaminants that may interfere with the biomass growth and/or lipid accumulation of the microorganism. Performing the fermentation under sterile conditions adds to the cost of the biological oil production from the microorganisms. In order to minimize the cost of fermentation, the present invention provides the unexpected solution of producing the biological oils by fermentation in nonsterile fermentors. The use of nonsterile fermentors to produce oil from a microorganism is especially suitable for production of oils for lipid-based biofuel purposes since it significantly reduces the costs of oil production and makes lipid-based biofuel production more commercially viable. Nonsterile fermentors may be used to produce biological oils with high or low polyunsaturated fatty acid content, depending on the requirements for a specific application.

Preferably, low-cost fermentors could be employed in the fermentations, including fiber reinforced polymer fermentors, metal matrix composite fermentors, ceramic matrix composite fermentors, thermoplastic composite fermentors, metal fermentors, epoxy lined carbon steel fermentors, plastic lined carbon steel fermentors, plastic fermentors, fiberglass fermentors, concrete fermentors, and fermentors made of polymers (such as polypropylene (PP), high density polyethelene (HDPE), polycarbonate (PC), polystyrene (PS), polyvinyl chloride (PVC), kynar, and nylon). The low-cost fermentor can also be made of a combination of the above materials. Low-cost tank cleaning can also be employed in accordance with the present invention to further reduce costs of fermentation. Low-cost tank cleaning include, but is not limited to, using methoxide or ethoxide to chemically scrub the fermentation tanks.

In some embodiments of the present invention, the biological oil is produced at a rate of about 5 g/L/day to about 70 g/L/day in a nonsterile fermentor. Preferably, the amount of biological oil produced in a nonsterile fermentor is at least about 5 g/L/day, at least about 10 g/L/day, at least about 20 g/L/day, at least about 30 g/L/day, at least about 40 g/L/day, at least about 50 g/L/day, at least about 60 g/L/day, or at least about 70 g/L/day. In some embodiments of the present invention, the amount of biological oil produced in a nonsterile fermentor is from about 10 g/L/day to about 70 g/L/day, from about 20 g/L/day to about 70 g/L/day, or from about 30 g/L/day to about 70 g/L/day.

The growing of the microorganism in a nonsterile fermentor preferably achieves a high cell density of at least about 10 g/L, at least about 15 g/L, at least about 20 g/L, at least about 25 g/L, at least about 30 g/L, at least about 50 g/L, at least about 75 g/L, at least about 100 g/L, at least about 125 g/L, at least about 135 g/L, at least about 140 g/L, at least about 145 g/L, at least about 150 g/L, or at least about 200 g/L. In some embodiments of the present invention, the microorganisms undergoing fermentation in a nonsterile fermentor are capable of achieving a cell density of from about 10 g/L to about 300 g/L, from about 15 g/L to about 300 g/L, from about 20 g/L to about 300 g/L, from about 25 g/L to about 300 g/L, from about 30 g/L to about 300 g/L, from about 50 g/L to about 300 g/L, from about 75 g/L to about 300 g/L, from about 100 g/L to about 300 g/L, from about 125 g/L to about 300 g/L, from about 130 g/L to about 290 g/L, from about 135 g/L to about 280 g/L, from about 140 g/L to about 270 g/L, from about 145 g/L to about 260 g/L, or from about 150 g/L to about 250 g/L.

In some embodiments of the present invention, changes in the fermentation conditions of the microorganism (such as pH, temperature, dissolved oxygen concentration, ion ratios, etc.) can be utilized to alter the fatty acid profile of the resulting oil depending on the intended use of the biological oil. In accordance with the intended use of the biological oils of the present invention, fermentation conditions can be adjusted, for example, to promote or impede the production of lipids in the triglyceride form by the microorganisms, to promote or impede the production of specific fatty acids or blends of fatty acids by the microorganisms (such as fatty acids of a specific chain length or degree of unsaturation), to promote or impede the production of oils that provide a high or low level of energy per unit volume of the oil, or to promote or impede the accumulation of certain byproducts in the oils produced by the microorganisms. Different uses of the biological oils of the present invention for lipid-based biofuel purposes include, but are not limited to, uses as heating oil, transportation biodiesel, jet fuel, and fuel additives. In some embodiments of the present invention, deuterium can be utilized in the fermentation medium to facilitate production of ultra-low volume, very high value, specialty fuels or lubricants. In some embodiments of the present invention, the conversion of biological oils into lipid-based biofuels involves chemical processes and refining techniques known in the art which may also produce or be used to produce specialty chemical compounds similar to petroleum distillates (such as plastics components). The profit from the sale of these specialty chemicals could also offset the costs of lipid-based biofuels production. Various other uses of the biological oils are contemplated within the scope of the present invention. For example, the biological oils of the present invention can be used in any suitable food, nutritional, or pharmaceutical products.

The present invention also provides methods for fermenting the microorganisms in fermentation tanks that are submerged in a liquid such as water for cooling. In some embodiments of the present invention, the fermentation utilities can be set up in series to minimize energy use. For example, cooling effluent and sparge exhaust from one series of fermentors could be used as a supply (or partial supply) of cooling water and gas, respectively, for fermentors that are next in line in the series or upstream in the series. The fermentation system can be set up such that the cooling water could come from a natural body of water such as a lake, pond, or ocean. The fermentation system can be designed such that the cooling systems for the fermentors are connected in series such that the cooling water effluent from a first fermentor or a set of fermentors that are in the series can be used as a cooling water supply for a second fermentor or set of fermentors in the series. Similarly, the fermentation system can be designed such that the gas supply for the fermentors are connected in series such that the sparge exhaust from a first fermentor or a set of fermentors that are in the series can be used as a gas supply for a second fermentor or set of fermentors in the series. The first fermentor or set of fermentors can be earlier or later in the series in relation to the second fermentor or set of fermentors. The fermentations of the present invention are preferably conducted in batch, fed-batch, semi-continuous, or continuous modes.

While in some embodiments of the invention, the biological oils comprising triglycerides can be a crude oil (discussed in more detail below), other such oils useful in the present invention can be recovered from their sources by any suitable means known to those in the art. For example, oils can be recovered by extraction with solvents such as chloroform, hexane, methylene chloride, methanol and the like, by supercritical fluid extraction, or by solventless extraction methods. In some embodiments of the present invention, the biological oils are recovered by extraction with hexane. Alternatively, the oils can be extracted using extraction techniques, such as are described in U.S. Pat. No. 6,750,048 and PCT Patent Application Serial No. US01/01806, both filed Jan. 19, 2001, and entitled "Solventless Extraction Process," both of which are incorporated herein by reference in their entirety. Additional extraction and/or purification techniques are taught in PCT Patent Application Serial No. PCT/IB01/00841 entitled "Method for the Fractionation of Oil and Polar Lipid-Containing Native Raw Materials" filed Apr. 12, 2001; PCT Patent Application Serial No. PCT/IB01/00963 entitled "Method for the Fractionation of Oil and Polar Lipid-Containing Native Raw Materials Using Water-Soluble Organic Solvent and Centrifugation" filed Apr. 12, 2001; U.S. Provisional Patent Application Ser. No. 60/291,484 entitled "Production and Use of a Polar Lipid-Rich Fraction Containing Stearidonic Acid and Gamma Linolenic Acid from Plant Seeds and Microbes filed May 14, 2001; U.S. Provisional Patent Application Ser. No. 60/290,899 entitled "Production and Use of a Polar-Lipid Fraction Containing Omega-3 and/or Omega-6 Highly Unsaturated Fatty Acids from Microbes, Genetically Modified Plant Seeds and Marine Organisms" filed May 14, 2001; U.S. Pat. No. 6,399,803 entitled "Process for Separating a Triglyceride Comprising a Docosahexaenoic Acid Residue from a Mixture of Triglycerides" issued Jun. 4, 2002 filed Feb. 17, 2000; and PCT Patent Application Serial No. US01/01010 entitled "Process for Making an Enriched Mixture of Polyunsaturated Fatty Acid Esters" filed Jan. 11, 2001; all of which are incorporated herein by reference in their entirety. The extracted oils can be evaporated under reduced pressure to produce a sample of concentrated oil material. Processes for the enzyme treatment of biomass for the recovery of lipids are disclosed in U.S. Provisional Patent Application No. 60/377,550, entitled "HIGH-QUALITY LIPIDS AND METHODS FOR PRODUCING BY ENZYMATIC LIBERATION FROM BIOMASS," filed on May 3, 2002; PCT Patent Application Serial No. PCT/US03/14177 entitled "HIGH-QUALITY LIPIDS AND METHODS FOR PRODUCING BY ENZYMATIC LIBERATION FROM BIOMASS," filed on May 5, 2003; copending U.S. patent application Ser. No. 10/971,723, entitled "HIGH-QUALITY LIPIDS AND METHODS FOR PRODUCING BY LIBERATION FROM BIOMASS," filed on Oct. 22, 2004; EP Patent Publication 0 776 356 and U.S. Pat. No. 5,928,696, both entitled "Process for extracting native products which are not water-soluble from native substance mixtures by centrifugal force," the disclosures of which are hereby incorporated herein by reference in their entirety. The oils may be extracted by pressing.

In some embodiments, an oil obtained from a source described above can serve as the starting material for further modifications (such as transesterification or cracking) in accordance with the methods of the present invention even when it has not been subjected to conventional processing. Examples of such conventional processes that may be avoided include refining (e.g., physical refining, silica refining or caustic refining), desolventization, deodorization, winterization, chill filtration, and/or bleaching. Thus, in certain embodiments, the oils containing triglycerides have not been subjected to one or more treatments selected from refining, desolventization, deodorization, winterization, chill filtration, and bleaching and in further embodiments, the oils have not been subjected to any one of refining, desolventization, deodorization, winterization, chill filtration, and bleaching.

In some embodiments, the crude oil may be isolated from a microorganism using standard techniques, without being subjected to further refinement or purification. For example, the oil can be a microbial oil that has only been subjected to solvent extraction, such as hexane extraction, isopropanol extraction, or the like. In some embodiments of the present invention, the crude oil may be isolated from a microorganism using physical and/or mechanical extraction methods (such as through the use of a homogenizer, or by pressing), without being subjected to further refinement or purification.

In other embodiments, compositions comprising triglycerides having polyunsaturated fatty acid residues, such as oils described above, may be subjected to further processing steps, such as refining, desolventization, deodorization, winterization, chill filtration, and/or bleaching. Such "processed" oils include microbial oils that have been subjected to solvent extraction and one or more of these additional processing steps. In some embodiments, oils are minimally processed. "Minimally processed" oils include microbial oils that have been subjected to solvent extraction and filtration. In certain embodiments, minimally processed oils are further subjected to winterization.

In some embodiments of the present invention, a method similar to the FRIOLEX® (Westfalia Separator Industry GmbH, Germany) process is used to extract the biological oils produced by the microorganisms. FRIOLEX® is a water-based physical oil extraction process, whereby raw material containing oil can be used directly for extracting oil without using any conventional solvent extraction methods. In this process, a water-soluble organic solvent can be used as a process aid and the oil is separated from the raw material broth by density separation using gravity or centrifugal forces. Patent application publication nos. WO 01/76715 and WO 01/76385, the contents of which are incorporated herein by reference in their entirety, disclose such extraction methods.

After the oil has been extracted, the oil can be recovered or separated from non-lipid components by any suitable means known in the art. In preferred embodiments of the present invention, low-cost physical and/or mechanical techniques are used to separate the lipid-containing compositions from non-lipid compositions. For example, if multiple phases or fractions are created by the extraction method used to extract the oil, where one or more phases or fractions contain lipids, a method for recovering the lipid-containing phases or fractions can involve physically removing the lipid-containing phases or fractions from the non-lipid phases or fractions, or vice versa. In some embodiments of the present invention, a FRIOLEX® type method is used to extract the lipids produced by the microorganisms and the lipid-rich light phase is then physically separated from the protein-rich heavy phase (such as by skimming off the lipid-rich phase that is on top of the protein-rich heavy phase after density separation).

The biological oils produced by the microorganisms of the present invention can be recovered from autolysis or induced lysis of the microorganisms by exposing the microorganisms to a condition including, but not limited to, a certain pH, a certain temperature, the presence of an enzyme, the presence of a detergent, physical disruptions, or combinations thereof. In some embodiments of the present invention, a microorganism is exposed to such conditions that promote autolysis or induced lysis after producing oil in an amount of from about 30% to about 90% by weight of its dry biomass, from about 40% to about 90% by weight of its dry biomass, from about 50% to about 90% by weight of its dry biomass, from about 60% to about 90% by weight of its dry biomass, from about 65% to about 85% by weight of its dry biomass, from about 70% to about 85% by weight of its dry biomass, or from about 75% to about 80% by weight of its dry biomass. In further embodiments of the present invention, a microorganism is exposed to such conditions that promote autolysis or induced lysis after producing oil in an amount of at least about 30%, at least about 40%, at least about 50%, at least about 60%, at least about 70%, or at least about 75% by weight of its dry biomass. In some embodiments of the present invention, lysis or autolysis of the microorganisms is performed by the use of mechanical forces. In further embodiments of the present invention, the lysis or autolysis of the microorganisms is followed by mechanical separation of the lipids from the non-lipid compositions.

Suitable enzymes that can be used to induce lysis of the oil-producing microorganisms include, but are not limited to, commercially available enzymes or enzyme mixtures such as Proteinase K or Alcalase. The genetic modification of a microorganism to introduce activities of an enzyme that induces lysis of another microorganism or that induces autolysis is contemplated within the scope of the present invention. In some embodiments of the present invention, the oil-producing microorganisms undergo induced lysis in the presence of a detergent such as ionic (cationic or anionic) detergents, nonionic detergents, zwitterionic detergents, or combinations thereof. In further embodiments of the present invention, physical disruption methods such as mechanical grinding, liquid homogenization, use of high frequency sound waves in sonication, freeze/thaw cycles methods, pressing, extruding, or milling can be used to induce lysis of the oil-producing microorganisms. Preferably, the extraction of the oils will take place in the fermentors at the end of the fermentation by in-tank lysis of the oil-producing microorganisms.

Once the biological oils are produced in accordance with the present invention, various methods known in the art can be used to transform the biological oils into esters of fatty acids for use as biodiesel, jet biofuel, or as ingredients for food or pharmaceutical products. In some embodiments of the present invention, the production of esters of fatty acids comprises transesterifying the biological oils produced by the microorganism. In some embodiments of the present invention, the extraction of the oil from the microorganisms and the transesterification of the oil can be performed simultaneously, in a one step method. For example, the culture containing the oil-producing microorganisms can be exposed to conditions or treatments (or a combination of conditions or treatments) that promote both extraction of the oil and the transesterification of the oil. Such conditions or treatments could include, but are not limited to, pH, temperature, pressure, the presence of solvents, the presence of water, the presence of catalysts or enzymes, the presence of detergents, and physical/mechanical forces. Two sets of conditions or treatments could be combined to produce a one step method of extracting and transesterifying the oil, where one set of conditions or treatments favorably promotes extraction of the oil and the other set of conditions or treatments favorably promotes transesterification of the oil, so long as the two sets of conditions or treatments can be combined without causing significant reduction in the efficiency of either the extraction or the transesterification of the oil. In some embodiments of the present invention, hydrolysis and transesterification can be performed directly of whole-cell biomass. In other embodiments of the present invention, the extraction of the oil is performed as a step that is separate from the step of transesterification of the oil.

Preferably, such transesterification reactions are performed using acid or base catalysts. In some embodiments of the present invention, methods for transesterifying the biological oils into esters of fatty acids for use as biodiesel or as ingredients for food or pharmaceutical products involve reacting the biological oils containing triglycerides in the presence of an alcohol and a base to produce esters of the fatty acid residues from the triglycerides.

Alcohols suitable for use in the present invention include any lower alkyl alcohol containing from 1 to 6 carbon atoms (i.e., a $C_{1-6}$ alkyl alcohol, such as methyl, ethyl, isopropyl, butyl, pentyl, hexyl alcohols and isomers thereof). Without being bound by theory, it is believed that in some embodiments of the present invention, the use of lower alkyl alcohols in the methods of the present invention produces lower alkyl esters of the fatty acid residues. For example, the use of ethanol produces ethyl esters. In certain embodiments, the alcohol is methanol or ethanol. In these embodiments, the fatty acid esters produced are a methyl ester and an ethyl ester of the fatty acid residue, respectively. In processes of the present invention, the alcohol typically comprises from about 5 wt. % to about 70 wt. %, from about 5 wt. % to about 60 wt. %, from about 5% to about 50 wt. %, from about 7 wt. % to about 40 wt. %, from about 9 wt. % to about 30 wt. %, or from about 10 wt. % to about 25 wt. % of the mixture of the oil composition, the alcohol and the base. In certain embodiments, the composition and the base can be added to either pure ethanol or pure methanol. In general, the amount of alcohol used may vary with the solubility of the oil or composition containing triglycerides in the alcohol.

Any base known in the art to be suitable for use as a reactant may be used in the present invention. Bases of the formula RO-M, wherein M is a monovalent cation and RO is an alkoxide of a $C_{1-6}$ alkyl alcohol are particularly suited for the present invention. Examples of suitable bases include elemental sodium, sodium methoxide, sodium ethoxide, potassium methoxide, and potassium ethoxide. In some embodiments, the base is sodium ethoxide. In processes of the present invention, the base is typically added in an amount of from about 0.05 to about 2.0 molar equivalents of triglycerides, from about 0.05 to about 1.5 molar equivalents of triglycerides, from about 0.1 to about 1.4 molar equivalents of triglycerides, from about 0.2 to about 1.3 molar equivalents of triglycerides, or from about 0.25 to about 1.2 molar equivalents of triglycerides to the reaction step with the composition and the alcohol.

The composition comprising triglycerides, the alcohol and the base are reacted together at a temperature and for an amount of time that allows the production of an ester from the fatty acid residues and the alcohol. Suitable reaction times and temperatures may be determined by one of skill in the art to produce an ester. Without intending to be bound by theory, the fatty acid residues are believed to be cleaved from the glycerol backbone of the triglyceride and esters of each fatty acid residue are formed during the step of reacting. In certain embodiments, the step of reacting the composition in the presence of an alcohol and a base is performed at a temperature from about 20° C. to about 140° C., from about 20° C. to about 120° C., from about 20° C. to about 110° C., from about 20° C. to about 100° C., or from about 20° C. to about 90° C. In further embodiments, the step of reacting the composition in the presence of an alcohol and a base is performed at a temperature of at least about 20° C., 75° C., 80° C., 85° C., 90° C., 95° C., 105° C., or 120° C. In some embodiments of the present invention, the step of reacting the composition in the presence of an alcohol and a base is performed at a temperature of about 20° C., 75° C., 80° C., 85° C., 90° C., 95° C., 105° C., or 120° C. In some embodiments, the step of reacting the composition in the presence of an alcohol and a base is performed for a time from about 2 hours to about 36 hours, from about 3 hours to about 36 hours, from about 4 hours to about 36 hours, from about 5 hours to about 36 hours, or from about 6 hours to about 36 hours. In certain embodiments, the step of reacting the composition in the presence of an alcohol and a base is performed for about 0.25, 0.5, 1.0, 2.0, 4.0, 5.0, 5.5, 6, 6.5, 7, 7.5, 8, 8.5, 10, 12, 16, 20, 24, 28, 32, or 36 hours In one embodiment, the step of reacting the oil composition, alcohol and base may be conducted by refluxing the components to produce the fatty acid esters, such as PUFA esters. In additional embodiments, the step of reacting the oil composition may be carried out at a temperature that does not result in the refluxing of the reaction components. For example, carrying out the step of reacting the oil composition under pressures greater than atmospheric pressure can increase the boiling point of the solvents present in the reaction mixture. Under such conditions, the reaction can occur at a temperature at which the solvents would boil at atmospheric pressure, but would not result in the refluxing of the reaction components. In some embodiments, the reaction is conducted at a pressure from about 5 to about 20 pounds per square inch (psi); from about 7 to about 15 psi; or from about 9 to about 12 psi. In certain embodiments, the reaction is conducted at a pressure of 7, 8, 9, 10, 11, or 12 psi. Reactions conducted under pressure may be carried out at the reaction temperatures listed above. In some embodiments, reactions conducted under pressure may be carried out at at least about 70° C., 75° C., 80° C., 85° C., or 90° C. In some embodiments, reactions conducted under pressure may be carried out at 70° C., 75° C., 80° C., 85° C., or 90° C.

The reaction mixture comprising fatty acid esters can be further processed to obtain the fatty acid esters from the mixture. For example, the mixture may be cooled, diluted with water, and the aqueous solution extracted with a solvent such as hexane to produce a composition comprising fatty acid esters. Techniques for washing and/or extracting crude reaction mixtures are known in the art.

In some embodiments of the present invention, microorganisms that produce low levels of PUFAs are used to produce the biological oils, especially for use in biodiesel production. This method could reduce the costs of biodiesel production. In some embodiments of the present invention, less than about 50% of unsaturated fatty acids in the biological oil are PUFAs. For certain biofuel applications, the unsaturated fatty acids in the biological oil preferably contains less than about 40%, less than about 30%, less than about 20%, less than about 10%, or less than about 5% PUFAs. In some embodiments of the present invention, the biological oil comprises less than about 50%, less than about 40%, less than about 30%, less than about 20%, less than about 10%, or less than about 5% by weight of PUFAs.

The more valuable PUFA esters can be recovered by distillation to yield high potency PUFA esters which can then be sold to reduce the overall cost of production of a biodiesel product.

Examples of modified lipid production systems are disclosed in patent application publication nos. WO 06/031699, US 2006/0053515, US 2006/0107348, and WO 06/039449, the contents of which are incorporated herein by reference in their entirety.

In one embodiment of the present invention, fatty acid esters are separated from the reaction mixture by distilling the composition to recover a fraction comprising the ester of the fatty acid. In this manner, a targeted fraction of the reaction mixture including the fatty acid esters of interest can be separated from the reaction mixture and recovered.

In certain embodiments, the distillation is performed under vacuum. Without being bound by theory, distillation under vacuum allows the distillation to be accomplished at a lower temperature than in the absence of a vacuum and thus may prevent the degradation of the esters. Typical distillation temperatures range from about 120° C. to about 170° C. In some embodiments, the step of distilling is performed at a temperature of less than about 180° C., less than about 175° C., less than about 170° C., less than about 165° C., less than about 160° C., less than about 155° C., less than about 150° C., less than about 145° C., less than about 140° C., less than about 135° C., or less than about 130° C. Typical pressures for vacuum distillation range from about 0.1 mm Hg to about 10 mm Hg. In some embodiments, the pressure for vacuum distillation is at least about 0.1, 0.5, 1, 1.5, 2, 2.5, 3, 3.5, or 4 mm Hg. In some embodiments of the present invention, the pressure for vacuum distillation is about 0.1, 0.5, 1, 1.5, 2, 2.5, 3, 3.5, or 4 mm Hg.

In some embodiments of the present invention, the fatty acid esters produced through transesterification of the biological oils are further isolated through urea adduction. Urea can be dissolved in a medium comprising the fatty acid esters to form a medium comprising fatty acid esters and dissolved urea. This medium is then cooled or concentrated to form a precipitate comprising urea and at least a portion of the saturated fatty acid esters, and a liquid fraction comprising at least most of the polyunsaturated fatty acid esters. The precipitate and liquid fraction can then be separated to isolate the saturated or polyunsaturated fatty acid esters. In some embodiments of the present invention, the medium comprising fatty acid esters and dissolved urea is cooled to a temperature of from about 20° C. to about −50° C., from about 10° C. to about −40° C., or from about 0° C. to about −30° C. U.S. Pat. No. 6,395,778, the content of which is incorporated herein by reference in its entirety, discloses methods of transesterification followed by urea adduction.

In addition to transesterification methods described above, other techniques of reducing the viscosity of the biological oils of the present invention can also be incorporated into the methods of the invention to produce lipid-based biofuels. These techniques include, but are not limited to, the use of lipases, supercritical methanol catalysis, and the use of whole-cell systems involving cytoplasmic overexpression of lipases in a host cell followed by permeabilization of the host to allow catalysis of transesterification of triglycerides within the cytoplasm. Patent or patent application publication nos. U.S. Pat. No. 7,226,771, US 2004/0005604, WO 03/089620, WO 05/086900, US 2005/0108789, WO 05/032496, WO 05/108533, U.S. Pat. No. 6,982,155, WO 06/009676, WO 06/133698, WO 06/037334, WO 07/076163, WO 07/056786, and WO 06/124818, the contents of which are incorporated herein by reference in their entirety, disclose examples of processes for converting lipids into biodiesel.

Thraustochytrids in general and *Schizochytrium* in particular are similar to many marine and estuarine microalgae and protists in that they accumulate a certain amount of polyunsaturated fatty acids (PUFA) in their cellular lipids. Low levels of PUFA may be useful as they should lower the gelling point of the fuel making it more suitable for cold climates. Potential consumer complaints about odors generated from burning PUFA-containing biodiesel in inefficient engines (that pass partially-oxidized fuel into the exhaust) may be somewhat offset by the fact that microalgal biodiesel fuel can be blended with fossil diesel at ratios of 1-99% to minimize this problem. To ensure that 100% microalgal oil-derived biodiesel could be burned without significant consumer issues, partial or total oil hydrogenation, as is routine in the manufacture of margarines, may be used. In some embodiments of the present invention, cracking technology (such as cracking methods known in the oil industry) can be used to reduce fatty acid chain length. Once the biological oil has been produced in accordance with methods of the present invention, cracking of the biological oil may be performed to produce the desired lipid-based biofuel. For certain lipid-based biofuels where a variety of shorter hydrocarbons are required, such as for jet biofuels, high levels of PUFAs may be useful so that cleavage of PUFA at multiple sites can occur to produce the various hydrocarbons.

The lipid-based biofuel compositions of the present invention are produced at low costs and are efficient replacements for petroleum diesel or jet fuel. In some embodiments of the present invention, the lipid-based biofuel composition comprises from about 1% to about 75% by weight of alkyl esters of long chain PUFAs having 20 or more carbons. In further embodiments of the present invention, the biodiesel composition comprises from about 2% to about 50%, from about 4% to about 25%, or from about 5% to about 10% by weight of alkyl esters of long chain PUFAs having 20 or more carbons.

In some embodiments of the present invention, the lipid-based biofuel compositions (100% lipid-based biofuel, not blended with petroleum diesel or jet fuel) have a melting temperature of from about 30° C. to about −60° C., from about 30° C. to about −50° C., from about 25° C. to about −50° C., from about 20° C. to about −30° C., from about 20° C. to about −20° C., from about 20° C. to about −10° C., from about 10° C. to about −10° C., or from about 0° C. to about −10° C. In further embodiments of the present invention, the biodiesel compositions releases from about 30 to about 45 megajoules per liter, from about 35 to about 40 megajoules per liter, or from about 38 to about 40 megajoules per liter. Various forms of biodiesel are disclosed, for example, in patent or patent application publication nos. WO 07/061903, U.S. Pat. No. 7,172,635, EP 1 227 143, WO 02/38709, WO 02/38707, and US 2007/0113467, the contents of which are incorporated herein by reference in their entirety.

The present invention also provides a scalable lipid-based biofuel manufacturing facility which may be co-located with an ethanol production facility (such as a cellulosic ethanol facility). Examples of algae systems related to the production of non-lipid based fuels (such as ethanol) are disclosed in patent or patent application publication nos. U.S. Pat. No. 7,135,308 and WO 02/05932, the contents of which are incorporated herein by reference in their entirety.

In some embodiments of the present invention, feedstock treatment would be similar or identical for both cellulosic ethanol and for cellulosic lipid-based biofuels fermentations. For example, after a cellulosic biodiesel fermentation, oil may be extracted and transesterified (either simultaneously or sequentially) to make biodiesel. The alcohol used in the transesterification could come from an ethanol production process (such as a cellulosic ethanol production process), and the left-over glycerol from the biodiesel transesterification could be used as a supplementary carbon source for the ethanol fermentation process (or for the biodiesel process itself, since organisms such as *Schizochytrium* readily metabolize glycerol). In preferred embodiments of the present invention, microorganisms used in the invention are capable of using glycerol as a carbon source. Nitrogenous wastes (such as yeast biomass) may also serve as nitrogen sources in biodiesel fermentations (most thraustochytrids can utilize yeast extract as a nitrogen source). Wastes such as de-lipidated microorganism biomass may be recycled for use in a subsequent fermentation, burned for heat or electricity, or used as fertilizer for the crop providing the cellulosic feedstock. The resulting biodiesel or waste gasses can be used to fuel the biodiesel or ethanol production facilities, making them energy independent. Additionally, pumps in the facility could be driven by recovered exhaust air.

In some embodiments of the present invention, the method of producing lipid-based biofuels comprises growing a microorganism using nutrients comprising recycled media to produce a biological oil. The recycled media include, but is not limited to, de-lipidated biomass, hydrolyzed biomass, partially hydrolyzed biomass, metals, salts, amino acids, extracellular carbohydrates, glycerol, recycled yeast biomass, or combinations thereof, all of which were recycled from a previous fermentation run or other process. For example, residual yeast biomass and hydrolyzed Stramenopile de-lipidated biomass waste can be recycled into the steam pre-treatment, ammonia fiber explosion, separation step, or into the enzyme hydrolysis, separation and evaporation step as shown in FIG. 1. Partially hydrolyzed biomass can be recycled back along with media into these steps for further hydrolysis. The use of recycled media may be employed for the production of biological oils with high or low polyunsaturated fatty acid content, depending on the requirements of a specific application.

The cellulose-based (low cost carbon) technology of the present invention can be used to lower the cost of production of any compound that can be produced by fermentation of yeasts or microorganisms of the kingdom Stramenopile (such as thraustochytrids), including genetically modified microorganisms. Examples of compounds that can be produced using the methods of the present invention include, but are not limited to, PUFAs, PUFA esters, proteins (including enzymes and therapeutic proteins), oxylipins, carotenoids, and lipids.

In some embodiments, the methods of the present invention may be used to produce compositions that contain a high percentage of PUFA or PUFA esters. For example, such compositions can contain from about 50 wt. % to about 100 wt. % of a PUFA or an ester of a PUFA, and in other embodiments, the composition can comprise at least about 50 wt. %, at least about 55 wt. %, at least about 60 wt. %, at least about 65 wt. %, at least about 70 wt. %, at least about 75 wt. %, at least about 80 wt. %, at least about 85 wt. %, at least about 90 wt. %, at least about 95 wt. %, at least about 99 wt. % of PUFAs or esters of PUFAs.

Compositions comprising PUFAs or PUFA esters of the present invention may be used in pharmaceutical products. In some embodiments, the pharmaceutical products may contain PUFAs or PUFA esters without an additional pharmaceutically active agent. In other embodiments, the pharmaceutical product may comprise a pharmaceutically active agent. Examples of pharmaceutically active agents include statins, anti-hypertensive agents, anti-diabetic agents, anti-dementia agents, anti-depressants, anti-obesity agents, appetite suppressants and agents to enhance memory and/or cognitive function. The pharmaceutical products may further comprises any pharmaceutically acceptable excipient, carriers, binders or other formulation components known in the art.

PUFAs or PUFA esters produced by the methods of the present invention are suitable for use as therapeutic and experimental agents. An embodiment of the present invention comprises the production of PUFAs or PUFA esters for treatment of PUFA-deficient infants. The PUFAs or PUFA esters can be included in a parenteral formulation that can be administered to an infant through parenteral routes to fortify the infant's supply of a PUFA. Preferred parenteral routes include, but are not limited to, subcutaneous, intradermal, intravenous, intramuscular and intraperitoneal routes. A parenteral formulation can include PUFAs or PUFA esters of the present invention and a carrier suitable for parenteral delivery. As used herein, a "carrier" refers to any substance suitable as a vehicle for delivering a molecule or composition to a suitable in vivo site of action. Examples of such carriers include, but are not limited to water, phosphate buffered saline, Ringer's solution, dextrose solution, serum-containing solutions, Hank's solution and other aqueous physiologically balanced solutions. Suitable carriers also include oil-based carriers, non-aqueous solutions, suspensions, and emulsions. Examples include propylene glycol, polyethylene glycol, vegetable oils such as olive oil, injectable organic esters such as ethyl oleate, polyethoxylated castor oil (cremaphor), and others known in the art. Acceptable protocols to administer PUFAs or PUFA esters in an effective manner include individual dose size, number of doses, frequency of dose administration, and mode of administration. Determination of such protocols can be accomplished by those skilled in the art depending upon a variety of variables, including the weight of the infant and the extent of PUFA deficiency. Another embodiment of the present invention comprises the production of PUFAs or PUFA esters for treatment of adults, in particular pregnant mothers. Acceptable protocols for administration of PUFAs or PUFA esters to adults includes parenteral feeding techniques or encapsulating PUFAs or PUFA esters of the present invention in a capsule, such as gelatin (i.e., digestible) capsule, for oral administration and/or in a liquid diet formulation. A liquid diet formulation can comprise a liquid composition containing nutrients suitable for supplementing a diet or nutrients sufficient as a complete diet.

PUFAs or PUFA esters produced by the methods of the present invention may also be used to treat subjects (e.g., humans or animals) with high levels of triglycerides, including subjects with triglyceridemia. For example, subjects with triglyceride levels at or above 500 mg/dL may benefit from treatment with the PUFAs or PUFA esters of the present invention. In some embodiments, individual PUFAs or PUFA esters may be administered to a subject to treat high levels of triglycerides. In certain embodiments, the PUFA or PUFA ester may be DHA or ARA. In other embodiments combinations of PUFAs or PUFA esters may be administered to a subject to treat high levels of triglycerides. In certain embodiments, the combination of PUFAs or PUFA esters may comprise omega-3 and omega-6 PUFAs such as DHA and DPA n-6. In some embodiments, the PUFAs or PUFA esters may comprise about 90% of a composition administered to the subject. The PUFAs or PUFA esters may be administered with other components and excipients, such as the carriers described above. The PUFAs or PUFA esters may also be used to treat subjects with diseases that can be associated with high levels of triglycerides, such as cardiovascular disease or hypertension.

The PUFA esters produced by the methods of the present invention may be used to produce PUFA salts. In some embodiments, PUFA salts can be produced by reacting the PUFA esters of the present invention in the presence of an alkaline metal base such as an alkaline metal hydroxide (e.g., potassium hydroxide). The PUFA salts formed from the PUFA esters of the present invention can be used in a variety of applications, such as in foods, beverages, and pharmaceuticals. In some embodiments, the PUFA salts produced using the PUFA esters of the present invention are water-soluble and can be used directly in foods, beverages, and pharmaceuticals.

PUFAs or PUFA esters produced by the methods of the present invention can be used in any animal food material, particularly food materials for humans, to create a food product having enhanced concentrations of PUFAs. The amount of fatty acids naturally in food products varies from one food product to another. A food product of the present invention can have a normal amount of a PUFA or a modified amount of a PUFA. In the former instance, a portion of the naturally occurring lipids may be substituted by PUFAs or PUFA esters of the present invention. In the latter instance, naturally occurring lipids may be supplemented by PUFAs or PUFA esters of the present invention.

PUFAs or PUFA esters may be added to foods for infants, such as infant formula and baby food. According to the present invention, an infant refers to infants and children less than about two years old, including, in particular, premature infants. Certain PUFAs are particularly important components of infant formula and baby food because of the rapid growth of infants (i.e., doubling or tripling in weight during the first year of life). An effective amount of PUFA or PUFA ester to supplement infant formula is an amount that approximates the concentration of the PUFAs in human breast milk. Preferred amounts of PUFAs or PUFA esters to add to infant formula or baby food range from about 0.1 to about 1.0% of total fatty acids, more preferably from about 0.1 to about 0.6% of total fatty acids, and even more preferably about 0.4% of total fatty acids.

Another aspect of the present invention includes a food product comprising a food material combined with PUFAs or PUFA esters of the present invention. PUFAs or PUFA esters may be added to a food material to create a food product having enhanced concentrations of PUFAs. As used herein, the term "food material" refers to any food type fed to humans or non-human animals. Also within the scope of the present invention is a method to make a food product comprising adding PUFAs or PUFA esters produced by methods of the present invention to a food material.

A suitable food material useful for the formation of a food product of the present invention includes animal food. The term "animal" means any organism belonging to the kingdom Animalia and includes, without limitation, primates (e.g., humans and monkeys), livestock and domestic pets. The term "food product" includes any product to be fed to such animals. Preferred food materials to be consumed by humans include infant formula and baby food. Preferred food materials to be consumed by domestic pets include dog foods.

PUFAs or PUFA esters produced by methods of the present invention can be added to a wide range of products such as baked goods, vitamin supplements, diet supplements, powdered drinks, etc. at various stages of production. Numerous finished or semi-finished powdered food products can be produced using the compositions of the present invention.

A partial list of food products comprising the products of the present invention includes doughs, batters, baked food items including, for example, such items as cakes, cheesecakes, pies, cupcakes, cookies, bars, breads, rolls, biscuits, muffins, pastries, scones, and croutons; liquid food products, for example, beverages, energy drinks, infant formula, liquid meals, fruit juices, multivitamin syrups, meal replacers, medicinal foods, and syrups; semi-solid food products such as baby food, yogurt, cheese, cereal, pancake mixes; food bars including energy bars; processed meats; ice creams; frozen desserts; frozen yogurts; waffle mixes; salad dressings; and replacement egg mixes. Also included are baked goods such as cookies, crackers, sweet goods, snack cakes, pies, granola/snack bars, and toaster pastries; salted snacks such as potato chips, corn chips, tortilla chips, extruded snacks, popcorn, pretzels, potato crisps, and nuts; specialty snacks such as dips, dried fruit snacks, meat snacks, pork rinds, health food bars and rice/corn cakes; and confectionary snacks such as candy.

Another product embodiment of the present invention is a medical food. A medical food includes a food which is in a formulation to be consumed or administered externally under the supervision of a physician and which is intended for the specific dietary management of a disease or condition for which distinctive nutritional requirements, based on recognized scientific principles, are established by medical evaluation.

The present invention, while disclosed in terms of specific methods, products, and organisms, is intended to include all such methods, products, and organisms obtainable and useful according to the teachings disclosed herein, including all such substitutions, modifications, and optimizations as would be available to those of ordinary skill in the art. The following examples and test results are provided for the purposes of illustration and are not intended to limit the scope of the invention.

EXAMPLES

Example 1

Using 2-liter fermentors, under typical fermentation conditions, cultures of a wild-type *Schizochytrium* or *Thraustochytrium* would be cultivated using a saccharified source of cellulose. Each fermentor would be batched with a media containing carbon (saccharfied cellulose), nitrogen, phosphorus, salts, trace metals, and vitamins. Each fermentor would be inoculated with a typical seed culture, then cultivated for 72-120 hours, and fed both a carbon (saccharified cellulose) feed and a nitrogen feed during cultivation. The nitrogen feed would be fed and consumed only during the growth phase, while the carbon (saccharified cellulose) would be fed and consumed throughout the fermentation. After 72-120 hours, each fermentor would be harvested and autolyzed or hydrolyzed. The hydrolyzed material would be separated into oil and biomass fractions. The oil would then be transesterified and separated from the glycerol. The mono alkyl ester would be water washed to produce a finished product.

Typical Fermentation Control Conditions:
Temperature: 20-40 degrees Celsius
pH: 3.0-10.0
agitation: 100-400 cps
airflow: 0.25-3.0 vvm
Saccharified cellulose: 5-35 g/L (in-tank concentration)
inoculum: 1%-50%

Example 2

Using 10-liter fermentors, under typical fermentation conditions, a culture of wild-type or transgenic *Schizochytrium* or *Thraustochytrium* would be cultivated on a liquefied cellulose source. The organism would produce the necessary enzymes to simultaneously saccharify the cellulose and metabolize the glucose, xylose, hemicellulose, and lignin. Each fermentor would be batched with a media containing carbon (liquefied cellulose), nitrogen, phosphorus, salts, trace metals, and vitamins. Each fermentor would be inoculated with a typical seed culture, then cultivated for 72-120 hours, and fed both a carbon feed (liquefied cellulose) and a nitrogen feed during cultivation. The nitrogen feed would be fed and consumed only during the growth phase, while the carbon (liquefied cellulose) would be fed and consumed throughout the fermentation. After 72-120 hours, each fermentor would be harvested and autolyzed or hydrolyzed. The hydrolyzed material would be separated into oil and biomass fractions. The oil would then be transesterified and separated from the glycerol. The mono alkyl ester would be water washed to produce a finished product.

Typical Fermentation Conditions:
Temperature: 20-40 degrees Celsius
pH: 3.0-10.0
agitation: 100-400 cps
airflow: 0.25-3.0 vvm
Liquefied cellulose: 5-35 g/L (in-tank concentration)
inoculum: 1%-50%

Example 3

The transgenic *Schizochytrium* or *Thraustochytrium* of Example 2 would be developed using an exiting transformation system (such as that disclosed in published patent application no. WO 2002/083869 A2) to express genes encoding known and appropriate cellulases, hemicellulases, ligninases, saccharide transporters, epimerases, and saccharide isomerases. Alternately, previously uncharacterized cellulases, hemicellulases, ligninases, saccharide transporters, epimerases, and saccharide isomerases could be isolated from existing genome databases or via standard gene discovery strategies with uncharacterized or less characterized organisms, including PCR with degenerate primers based on conserved regions of homologous genes, or mass sequencing and mining of Expressed Sequence Tags (ESTs) or genome sequences, or other techniques. Appropriate gene expression and gene product activities would be validated using standard techniques such as gel electrophoresis, northern and western blots, Enzyme-linked Immunosorbent Assays (ELISA), and substrate conversion assays.

Example 4

Using 2-liter fermentors, under typical fermentation conditions, two cultures of a wild-type *Schizochytrium* (ATCC 20888) were cultivated to compare the fatty acid profiles and lipid production rates under sterile and non-sterile conditions. Each fermentor was batched with a media containing carbon, nitrogen, phosphorus, salts, trace metals, and vitamins. The sterile fermentor was autoclaved for 120 minutes and all media components were either sterilized in the fermentor or added as sterile solutions after autoclaving. The non-sterile fermentor was batched with tap water and all ingredients were added to the fermentor without sterilization prior to inoculation. Each fermentor was inoculated with a typical seed culture, then cultivated for 50 hours, and fed both a carbon feed and a nitrogen feed during cultivation. The nitrogen feed was fed and consumed only during the growth phase, while the carbon was fed and consumed throughout the fermentation. After 50 hours, each fermentor was sampled, centrifuged, lyophilized, converted to fatty acid methyl ester, and analyzed by gas chromatography.
Typical Fermentation Conditions:
Temperature: 28-30 degrees Celsius
pH: 5.0-7.5
agitation: 100-300 cps
airflow: 0.25-2.0 vvm
glucose: 5-55 g/L (concentration)
inoculum: 1%-30%
The results were as follows:

| | condition | |
|---|---|---|
| | sterile | non-sterile |
| | strain | |
| | ATCC 20888 | ATCC 20888 |
| | log hour | |
| Sample | 50 BN25 8.08, 14 | 50 BN26 8.08, 14 |
| % 12:0 | 0.21 | 0.12 |
| % 13:0 | 0.16 | 0.16 |
| % 14:0 | 9.73 | 6.14 |
| % 15:1 | 0.59 | 0.79 |
| % 16:0 | 39.93 | 36.26 |
| % 16:1 | 0.13 | 0.07 |
| % 17:0 | 0.17 | 0.28 |
| % 18:0 | 1.13 | 1.16 |
| % 18:1 n-9 | 0.13 | 0.08 |
| % 18:1 n-7 | 0.10 | 0.00 |

| | condition | |
|---|---|---|
| | sterile | non-sterile |
| | strain | |
| | ATCC 20888 | ATCC 20888 |
| | log hour | |
| Sample | 50 BN25 8.08, 14 | 50 BN26 8.08, 14 |
| % 18:3 n-6 | 0.10 | 0.12 |
| % 18:3 n-3 | 0.04 | 0.07 |
| % 18:4 n-3 | 0.12 | 0.13 |
| % 20:0 | 0.10 | 0.10 |
| % 20:3 n-6 | 0.27 | 0.33 |
| % 20:4 ARA | 0.37 | 0.32 |
| % 20:5 EPA | 0.45 | 0.56 |
| % 22:5 n-6 | 12.61 | 14.52 |
| % 22:6 DHA | 32.67 | 37.43 |
| % Fat | 40.92 | 35.79 |
| % Unknown | 0.98 | 1.10 |
| % saturates | 51.44 | 44.23 |
| % monounsaturates | 0.81 | 0.87 |
| % polyunsaturates | 46.64 | 53.48 |

Figure 3:
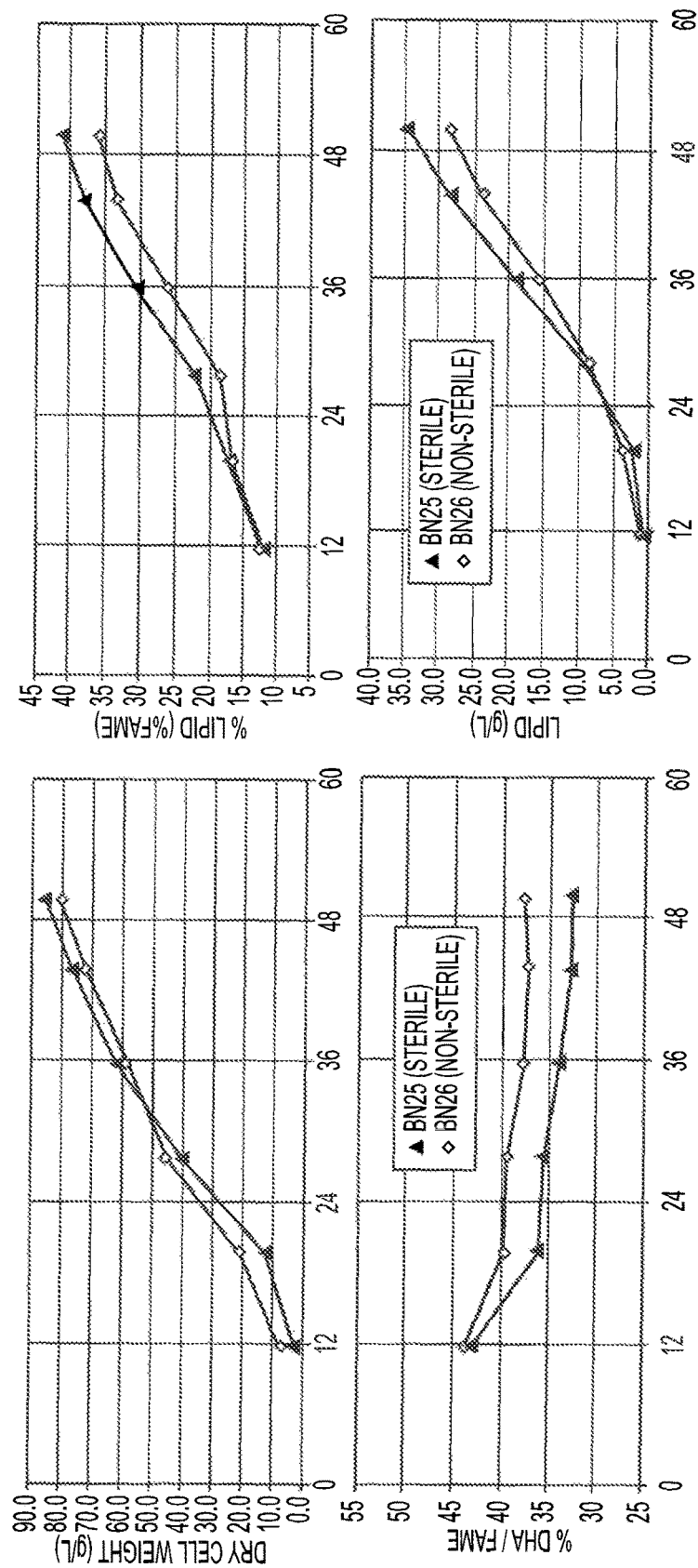
FIG. 3 shows graphs of the dry cell weight, percent by weight of lipids, percentage by weight of DHA, and amount of lipid produced per liter of fermentation broth over time for the growth of a microorganism (ATCC 20888) under sterile and nonsterile conditions described in Example 4.
Figure 4:
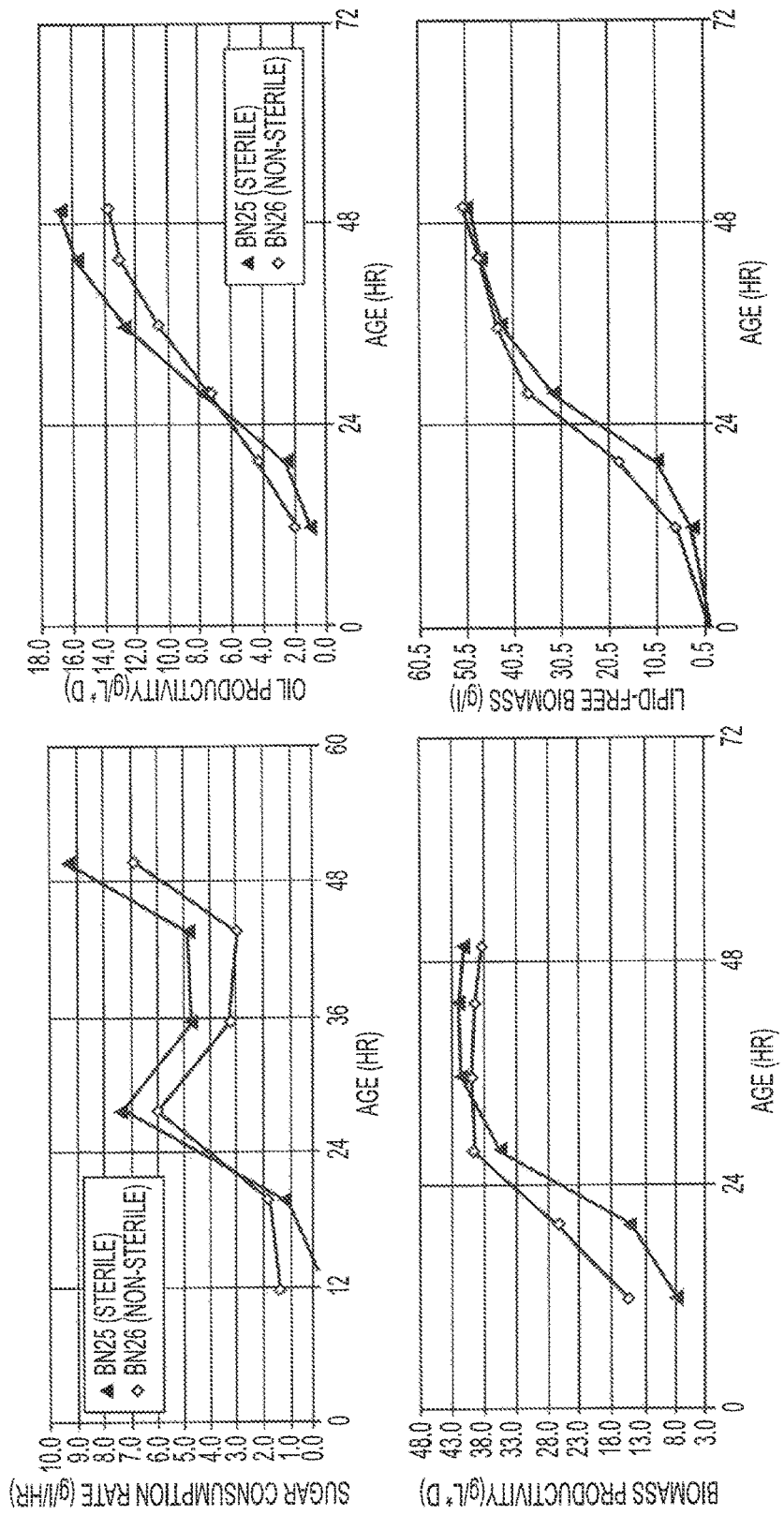
FIG. 4 shows graphs of the sugar consumption rate, oil production rate (as grams per liter of fermentation broth per day), biomass productivity rate (in grams per liter per day), and the amount of lipid-free biomass over time for the growth of a microorganism (ATCC 20888) under sterile and nonsterile conditions described in Example 4.
Figure 5:
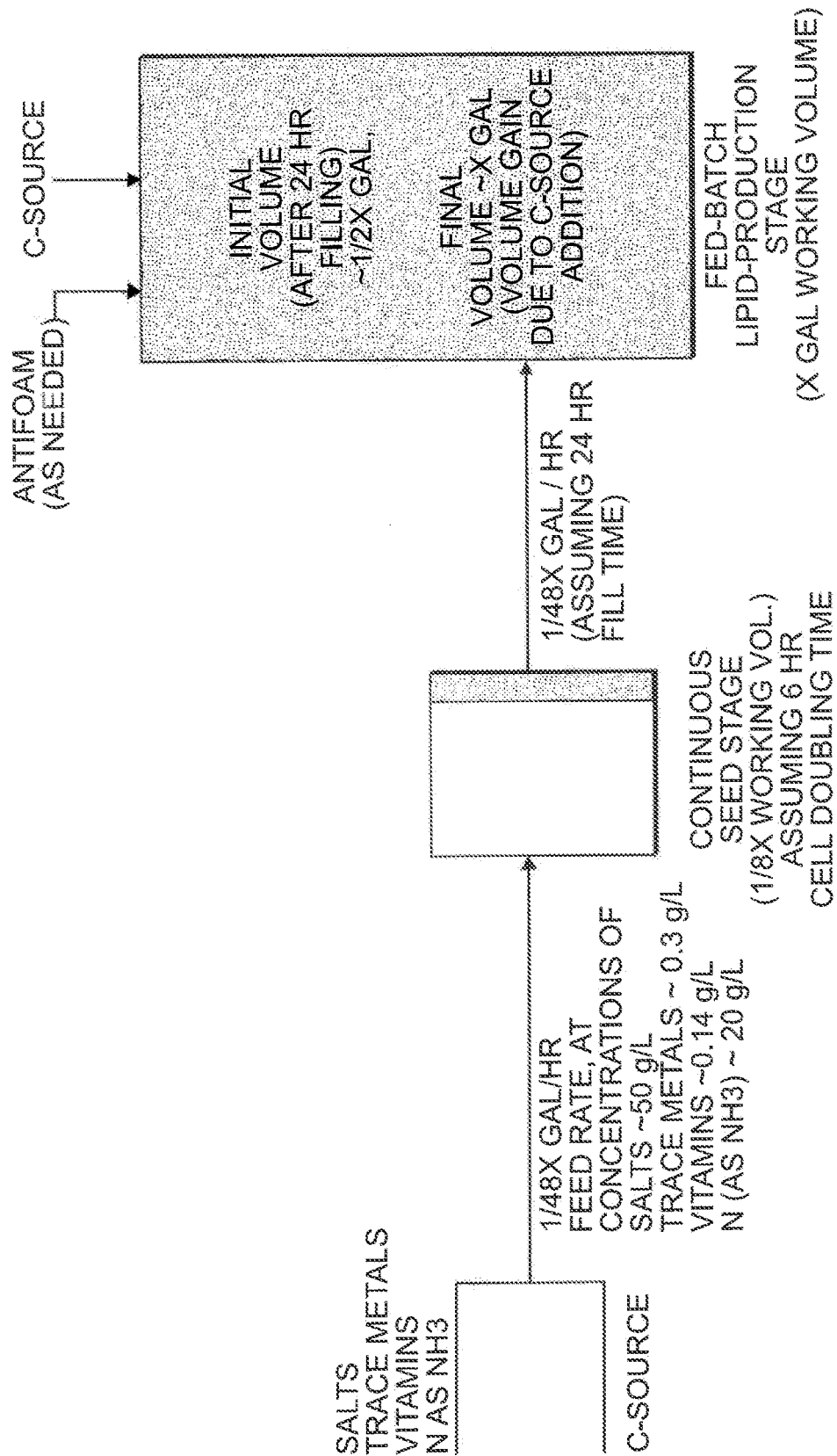
FIG. 5 shows a diagram of a two-stage fermentation process comprising a continuous seed stage and a fed-batch lipid accumulation stage.

FIGS. 3 and 4 show graphs of the results of the experiment.

Example 5

Using a 5-liter fermentor, under low-cost fermentation conditions wild-type *Schizochytrium* (ATCC 20888) was cultivated to evaluate the potential to produce algal biomass heterotrophically using low-cost non-sterile conditions. The non-sterile fermentor consisted of a mild steel vessel, lined with a polypropylene membrane, a tube sparger, one exhaust line, and one addition line. The non-sterile fermentor was batched with tap water and a media containing carbon, nitrogen, phosphorus, salts, trace metals, and vitamins. The ingredients were added to the fermentor without sterilization prior to inoculation. The fermentor was inoculated with a 50 mL culture from a 250 mL flask. The fermentor was cultivated for 6 days, nothing was added to the fermentor during cultivation (post-inoculation). After 6 days, the fermentor was sampled, lyophilized, converted to fatty acid methyl ester, and analyzed by gas chromatography.
Typical Fermentation Conditions:
Temperature: 28-30 degrees Celsius
pH: no control
agitation: none
airflow: 2.0-4.0 vvm
glucose: 80 g/L (initial concentration; no additional feeds)
inoculum: 1%
Non-Sterile Batch Media:

| Ingredient | Final Concentration |
|---|---|
| Na2SO4 | 8 g/L |
| KCl | 1 g/L |
| MgSO4•7H2O | 2 g/L |
| KH2PO4 | 12 g/L |
| (NH4)2SO4 | 15 g/L |
| CaCl2*2H2O | 0.2 g/L |
| FeSO4•7H2O | 51.5 mg/L |
| MnCl2•4H2O | 3.1 mg/L |
| ZnSO4•7H2O | 3.1 mg/L |
| CoCl2•6H2O | 0.04 mg/L |
| Na2MoO4•2H2O | 0.04 mg/L |
| CuSO4•5H2O | 2.07 mg/L |

-continued

| Ingredient | Final Concentration |
|---|---|
| $NiSO_4 \cdot 6H_2O$ | 2.07 mg/L |
| Thiamine | 9.75 mg/L |
| Vitamine B12 | 0.16 mg/L |
| $Ca_{1/2}$-pantothenate | 3.33 mg/L |
| Glucose | 80 g/L |

The results were as follows:

| | |
|---|---|
| % PUFA | 5.75 |
| % monounsaturates | 55.18 |
| % saturates | 37.19 |
| g/L oil | 4.64 |

Example 6

A two-stage fermentation system could be used in the heterotrophic fermentation of a microorganism. The first stage (seed stage) will target accumulation of biomass and the second stage (lipid-production stage) will target lipid accumulation. An example of the fermentation system is described below.

The fermentation system described below includes a continuous seed vessel and multiple lipid-production vessels running at fed-batch mode. The seed vessel has a working volume of xx gallons, an eighth of the lipid-production stage vessels' (xxx gallons) based on the following assumptions:
1) 6 hours of cell doubling time,
2) 24 hours fill-time for each lipid-production stage batch,
3) Initial volume (after filling) of each lipid-production batch being ½ of the harvest volume Continuous Seed Stage After the initial inoculation/growth to reach steady state, the seed vessel will receive continuous sterile nutrient feed at a constant rate (xx GPM, ~⅛ of harvest volume per hour). Broth will be withdrawn from the vessel and transferred to a lipid-production stage vessel at the same rate as the nutrient feed. After a production vessel reaches the desired starting volume (~½ of the harvest volume after ~24-hour filling), the seed vessel will then be connected to the next available lipid-production vessel.

The nutrient feed will include a carbon source (cellulosic feedstock and/or simple sugars), a nitrogen source (e.g. NH3), salts, vitamins and trace metals at concentrations to sustain appropriate growth (and later to support optimal lipid production). Recycled de-lipidated biomass and glycerol may be used as part of the nutrients to reduce raw material cost. At steady state, the biomass concentration will likely to reach at least about 50-100 g/L.

Airflow will be supplied to provide sufficient oxygen for cell growth. The airflow requirement could be in the range~0.5-1.0 vvm to achieve OUR (oxygen uptake rate) of ~50-150 mmoles/L/hr. Significant metabolic heat generation is expected for the process and sufficient heat removal will be required to maintain the target process temperature (e.g. ~25-35° C.). A relationship of 0.113 Kcal/mmole 02 uptake is commonly used to estimate metabolic heat generation by micro-organisms and an estimated heat generation of ~6-17 Kcal/L/hr may be produced. Some of the heat may be removed by airflow but significant heat removal capability will still be required to maintain the target temperature. pH control by an acid (e.g. sulfuric acid) and/or a base (caustic) may be required to maintain the pH target for optimal growth. Due to the nature of the seed stage, the medium and process conditions will very likely favor contaminant growth; and therefore, a system design with low contamination risk will be highly desirable. The two-stage process may be carried out in non-sterile fermentors through the selection of conditions that are unfavorable for contaminants. Another option is to run the continuous seed stage aseptically and the lipid-production stage (which can be under a nutrient limitation such as nitrogen limitation) under non-sterile conditions.

Lipid-Production Stage (Fed-Batch)

The lipid-production stage vessel will run as a fed-batch process. Most nutrients will be received from the seed stage (during the 24 hours fill time) and carbon source will be fed to the batch to maintain a target sugar concentration throughout the run.

Each lipid-production batch will have a total cycle time of 120 hour, 24 hours for filling (receiving broth from the seed vessel), 72 hours for lipid-production and 24 hours for harvest & turnaround. Therefore, each seed vessels should be able to supply inoculum for five lipid-production stage vessels. As mentioned above, the seed transfer rate is expected to be at ~xxx GMP (⅛ pf harvest volume per hour). After the 24 hour fill time, the production vessel should have around ½ of the target harvest volume. Carbon source, such as cellulosic feedstock (at ~70% sugar concentration), will be added to maintain a target sugar concentration through most of the run time. Anti-foam will be added as needed to minimize forming. At harvest, a biomass concentration of at least about 150 g/L or at least about 300 g/L, and 60-80% oil in biomass may be achieved.

A continuous or semi-continuous production strategy may be used for lipid production. In a continuous method, the biomass is harvested at the same rate that the lipid production vessel is filled. In a semi-continuous method, the biomass is harvested at regular intervals, with the amount of biomass harvested dependent on the lipid-production cycle. For example, in a 72 hour lipid-production cycle, half of the production tank containing biomass may be harvested every 36 hours; similarly, 25% of the biomass in the production tank may be harvested every 18 hours, 75% of the biomass in the production tank may be harvested every 54 hours, and so on.

Oxygen is required for cell maintenance and lipid-production and airflow will be supplied to provide sufficient oxygen transfer. The airflow requirement could be in the range~0.5-1.0 vvm to achieve OUR (oxygen uptake rate) of ~40-150 mmoles/L/hr. Significant metabolic heat generation is expected for the process. A relationship of 0.113 Kcal/mmole O2 uptake is commonly used to estimate metabolic heat generation by micro-organisms and an estimated heat generation of ~6-17 Kcal/L/hr may be produced. Some of the heat may be removed by airflow but significant heat removal capability will still be required to maintain the target temperature. pH control by an acid (e.g. sulfuric acid) and/or a base (caustic) may be required to maintain the pH target for high lipid productivity.

Other Information/Considerations

The cost of fermentation may be lowered if fermentation waste (such as liquid media or de-lipidated biomass) can be efficiently recycled.

The sugar to biomass conversion yield will likely be ~45-55% (on molar basis) and the sugar to oil conversion yield will likely be ~30-40%.

To minimize potential downtime due to equipment failure or batch abnormalities, additional seed and lipid-production vessels should be considered for plant design.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

What is claimed is:

1. A method for producing a biological oil comprising
(a) growing an oil-producing microorganism of the kingdom Stramenopile by heterotrophic fermentation in a medium comprising cellulose as a carbon source, and
(b) isolating or purifying the biological oil made in step (a); wherein about 11% to about 99% of unsaturated fatty acids in said biological oil are polyunsaturated fatty acids, and wherein said fermentation is performed in a fermentor selected from the group consisting of fiber reinforced polymer fermentors, metal matrix composite fermentors, ceramic matrix composite fermentors, thermoplastic composite fermentors, metal fermentors, epoxy lined carbon steel fermentors, plastic lined carbon steel fermentors, plastic fermentors, fiberglass fermenters, and concrete fermentors.

2. The method of claim 1, wherein greater than about 50% of unsaturated fatty acids in said biological oil are polyunsaturated fatty acids.

3. The method of claim 1, wherein said microorganism is a Thraustochytrid.

4. The method of claim 1, wherein said microorganism is selected from the group consisting of microorganisms of the genus *Schizochytrium*, microorganism of the genus *Thraustochytrium*, and microorganisms of the genus *Ulkenia*.

5. The method of claim 1, wherein said microorganism saccharifies said cellulose.

6. The method of claim 1, wherein said microorganism is resistant to or degrades feedstock components selected from the group consisting of lignin, hemicellulose, plant oil, plant extracellular polysaccharides, and combinations thereof.

7. The method of claim 1, wherein said microorganism is a genetically modified microorganism.

8. The method of claim 1, wherein said microorganism produces oil in triglyceride form in an amount of from about 25% to about 85% by weight of its dry biomass.

9. The method of claim 1, further comprising performing autolysis or induced lysis of said microorganism after said microorganism has produced oil in an amount of from about 30% to about 90% by weight of its dry biomass.

10. The method of claim 1, further comprising inducing lysis of said microorganism by exposing said microorganism to a condition favorable for lysis selected from the group consisting of a pH, a temperature, the presence of an enzyme, the presence of a detergent, physical disruption, and combinations thereof.

11. The method of claim 1, wherein said medium comprising cellulose comprises a source of cellulose selected from the group consisting of grass, sugar cane, agricultural waste, waste paper, sewage, wood, an organism of the kingdom viridiplantae, and combinations thereof.

12. The method of claim 1, wherein said fermentation is performed in a nonsterile fermentor.

13. The method of claim 1, wherein said fermentation is carried out in a fermentor that is submerged in water.

14. The method of claim 1, wherein said fermentation is carried out in fermentors having cooling systems connected in series such that cooling water effluent from a first fermentor or a set of fermentors in the series is used as a cooling water supply for a second fermentor or set of fermentors in the series.

15. The method of claim 1, wherein said fermentation is carried out in fermentors having gas systems connected in series such that sparge exhaust from a first fermentor or a set of fermentors in the series is used as a gas supply for a second fermentor or set of fermentors in the series.

* * * * *